(12) United States Patent
Shadduck

(10) Patent No.: US 7,264,351 B2
(45) Date of Patent: Sep. 4, 2007

(54) ADAPTIVE OPTIC LENS AND METHOD OF MAKING

(75) Inventor: John H. Shadduck, Tiburon, CA (US)

(73) Assignee: PowerVision, Inc., Belmont, CA (US)

( * ) Notice: Subject to any disclaimer, the term of this patent is extended or adjusted under 35 U.S.C. 154(b) by 0 days.

(21) Appl. No.: 11/214,538

(22) Filed: Aug. 29, 2005

(65) Prior Publication Data

US 2006/0061729 A1    Mar. 23, 2006

Related U.S. Application Data

(63) Continuation of application No. 10/795,166, filed on Mar. 6, 2004, now Pat. No. 6,935,743.

(60) Provisional application No. 60/453,010, filed on Mar. 6, 2003.

(51) Int. Cl.
G02C 7/02 (2006.01)

(52) U.S. Cl. ................................. 351/159; 351/160 R

(58) Field of Classification Search ................ 351/159, 351/160 R, 177; 359/665–667; 623/6.13, 623/6.22, 6.37
See application file for complete search history.

(56) References Cited

U.S. PATENT DOCUMENTS

| | | | |
|---|---|---|---|
| 4,253,199 A | 3/1981 | Banko | |
| 4,373,218 A | 2/1983 | Schachar | |
| 4,512,040 A | 4/1985 | McClure | |
| 4,585,457 A | 4/1986 | Kalb | |
| 4,685,921 A | 8/1987 | Peyman | |
| 4,685,922 A | 8/1987 | Peyman | |
| 4,693,717 A | 9/1987 | Michelson | |
| 4,731,078 A | 3/1988 | Stoy et al. | |
| 4,787,903 A | 11/1988 | Grendahl | |
| 4,816,031 A | 3/1989 | Pfoff | |
| 4,888,012 A | 12/1989 | Horn et al. | |
| 4,892,543 A | 1/1990 | Turley | |
| 4,902,293 A | 2/1990 | Feaster | |
| 4,932,966 A | 6/1990 | Christie et al. | |
| 4,950,289 A | 8/1990 | Krasner | |
| 4,994,082 A | 2/1991 | Richards et al. | |
| 5,035,710 A | 7/1991 | Nakada et al. | |
| 5,066,301 A * | 11/1991 | Wiley ........................ 623/6.13 |
| 5,145,935 A | 9/1992 | Hayashi | |
| 5,213,579 A | 5/1993 | Yamada et al. | |

(Continued)

FOREIGN PATENT DOCUMENTS

JP    9294754    11/1997

*Primary Examiner*—Scott J. Sugarman
*Assistant Examiner*—Darryl J. Collins
(74) *Attorney, Agent, or Firm*—Shay Law Group LLP

(57) ABSTRACT

An lens for correcting human vision, for example an IOL, contact lens or corneal inlay or onlay, that carries and interior phase or layer comprising a pattern of individual transparent adaptive displacement structures. In the exemplary embodiments, the displacement structures are actuated by shape change polymer that adjusts a shape or other parameter in response to applied energy that in turn displaces a fluid media within the lens that actuates a flexible lens surface. The adaptive optic means of the invention can be used to create highly localized surface corrections in the lens to correct higher order aberrations-which types of surfaces cannot be fabricated into and IOL and then implanted. The system of displacement structures also can provide spherical corrections in the lens.

5 Claims, 17 Drawing Sheets

U.S. PATENT DOCUMENTS 5,235,003 A    8/1993   Ward et al.
5,275,623 A    1/1994   Sarfarazi
5,288,293 A    2/1994   O'Donnell, Jr.

2002/0016629 A1    2/2002   Sandstedt et al.
2003/0003295 A1*   1/2003   Dreher et al. ............... 428/332

* cited by examiner

ADAPTIVE OPTIC LENS AND METHOD OF MAKING

REFERENCE TO RELATED APPLICATIONS

This application is a continuation of application Ser. No. 10/795,166, filed Mar. 6, 2004, now U.S. Pat. No. 6,935,743 which claims the benefit of U.S. Provisional Application No. 60/453,010, filed Mar. 6, 2003. All of the above applications are incorporated herein by this reference

FIELD OF THE INVENTION

The present invention pertains to an adaptive optic ophthalmic lens that allows for post-fabrication modification that allows for correction of higher order aberrations or spherical errors. More in particular, the invention can be used in IOLs, corneal inlay and onlays, contact lenses and the like wherein lens components respond to an external energy source, such as a laser, to allow adaptive structures at an interior of the lens to be altered in dimension to thereby adjust or flex the lens shape in a manner akin to methods used in the field of adaptive optics (AO) in astronomical telescopes.

BACKGROUND OF THE INVENTION

Post-fabrication adjustment of optical characteristics of lenses is needed in various ophthalmic lens types. In one case, cataract patients would benefit from post-implant power adjustability of an IOL implant. In another case, posterior chamber phakic IOLs could benefit from post-implant power adjustability since biometry cannot insure proper power selection. Corneal inlays or similar types of lens also would benefit from implantation of thin plano lenses followed by a later expansion of the lens to provide the desired refractive effect. Also, contact lenses would benefit from post-fabrication curvature adjustment to limit the number of lenses that needed to be maintained in inventories.

Cataracts are major cause of blindness in the world and the most prevalent ocular disease. Visual disability from cataracts accounts for more than 8 million physician office visits per year. When the disability from cataracts affects or alters an individual's activities of daily living, surgical lens removal with intraocular lens implantation is the preferred method of treating the functional limitations.

In the United States, about 2.5 million cataract surgical procedures are performed annually, making it the most common surgery for Americans over the age of 65. About 97 percent of cataract surgery patients receive intraocular lens implants, with the annual costs for cataract surgery and associated care in the United States being upwards of $4 billion.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age-related cataract conditions are the most common.

In treating a cataract, the surgeon removes material from the lens capsule and replaces it with an intraocular lens (IOL) implant. The typical IOL provides a selected focal length that allows the patient to have fairly good distance vision. Since the lens can no longer accommodate, the patient typically needs prescription eyeglasses for reading.

The surgeon selects the power of the IOL based on analysis of biometry of the patient's eye prior to the surgery. In a significant number or cases, after the patient's eye has healed from the cataract surgery, there is a refractive error was beyond the margin of error in the biometric systems. Thus, there remain intractable problems in calculating the proper power of an IOL for any particular patient. To solve any unpredicted refractive errors following IOL implantation, the ophthalmologist can perform a repeat surgery to replace the IOL—or the patient can live with the refractive error and may require prescription eyeglasses to correct for both near and distant vision.

The correction of ocular wavefront aberration in ophthalmology is a field of increasing interest. Current diagnostic systems based on the Shack-Hartmann (S-H) wavefront sensors can operate in real time, measuring the aberrations about every 40 msec. Besides the diagnostic speed provided, there are other advantages of these new devices in ocular wavefront aberration measurement, such as the use of infrared light, and the fact that the systems use objective methods to simplify the task of the subject.

At present, the only way to correct ocular aberrations beyond second-order is by customized refractive surgery such as in situ keratomileusis (LASIK). However, the corneal ablation approach will suffer from many problems such as the complexity of controlling corneal biomechanics and healing after surgery, and aberrations probably induced by cutting the corneal flap that enables the ablation procedure.

Preliminary research has been done in correcting aberrations with aspheric customized contact lenses. This approach also faces practically insurmountable problems relating to coupling lenses with eye aberrations: (i) lens flexure will be a problem; (ii) tear film effects will introduce spurious aberrations, and (iii) lens rotations and lens translation will limit the performance of the aberration correction.

In studies on large populations, it has been found that for a 5-mm pupil, the contribution to the total root mean square (RMS) wavefront error of the second order is approximately 70% in highly aberrated eyes and 90% in young healthy eyes. If a lens were provided that could correct include third order and spherical aberrations, the percentage of the population that could benefit from wavefront correction would increase to 90% for highly aberrated eyes and to 99% for normal eyes.

Zernike polynomials are a set of functions that are orthogonal over the unit circle. They are useful for describing the shape of an aberrated wavefront in the pupil of an optical system. Several different normalization and numbering schemes for these polynomials are in common use. Fitting a wavefront to Zernike polynomials allows lens designers to analyze the subcomponent aberrations contained in the total wavefront. Some of the lower order aberrations (also defined as Zernike polynomial coefficients having an order (e.g., to first through fifth order aberrations)) in a Zernike series are prism, sphere, astigmatism, coma, and spherical aberration.

A Zernike equation can include as many or few aberrations as required for an application, for example, with more than 63 aberrations beyond sphere. Further explanations of higher order aberration can be found in the following references: Macrae et al., Customized Corneal Ablation-The Quest for SuperVision, Slack Inc., Thorofare, N.J. (2001); Thibos et al., Standards for Reporting the Optical Aberrations of Eyes, Trends in Optics and Photonics Vol. 35, Vision Science and Its Applications, Vasudevan Lakshminarayanan, ed., Optical Society of America, Washington, D.C. (2000), pp. 232-244; Atchison et al., Mathematical Treatment of Ocular Aberrations: a User's Guide, (2000). For the purposes of this disclosure, the adaptive optic corresponding to the invention is designed for the optional correction of higher order aberrations ranging at least above third order aberrations.

In view of the foregoing, what is needed is a lens system that provides means for post-fabrication or post-implant adjustment of optical characteristics and dioptic power. What also is needed is a lens system that can correct higher order aberrations.

SUMMARY OF THE INVENTION

Of particular interest, the lens corresponding to the invention falls into the class of adaptive optics (AO) in the sense that micro-scale actuator means are provided to flex and alter the curvature of the lens surface locally for higher order aberrations or globally for spherical corrections, within a selected range of dimensions. The usual scope of the AO field encompasses flex-surface mirrors wherein piezoelectric or other drivers can flex the optical surface within microsecond intervals to reduce aberrations, for example in astronomical telescopes as shown in FIG. 1A.

The actuators of the present invention differ completely in that they only need be actuated one time, or perhaps a few times, and there is no need for rapid actuation response times. Still, the invention provides an AO structure wherein the adaptive optics comprise index-matched displacement structures at a micro-scale suitable for correcting higher order aberrations disposed in an interior of the lens. The actuators are in a fixed pattern in an interior lens phase with each having an index that matches the material of lens body, as indicated schematically in FIG. 1B.

In one preferred embodiment, the adaptive structure is responsive to localized energy application thereto, preferably in the form of light energy. In another embodiment, the actuator has an extending portion that extends to the lens periphery to allow higher energy densities to be used by providing a non-transmissive backing element.

A light source operating in the 400 nm to 1.4 micron range is suitable (not limiting) which will typically comprise a laser but other non-laser light sources fall within the scope of the invention. The light source is coupled to a computer controller, galvanometric scanner (or any other type of scanner), and optional eye-tracking system, all of which are known in the art (e.g., in LASIK systems) and for this reason need no further description for adjusting an IOL. The micro-actuator means, or more particularly the adaptive displacement structures are indicated in FIG. 1B, comprise a plurality of elements that define selected micron scale dimensions across principal and secondary axes thereof, wherein the structures engage at least one deformable lens surface layer. In a contact lens, the light source can be less complex and need not be scanned as will be described below.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1A:
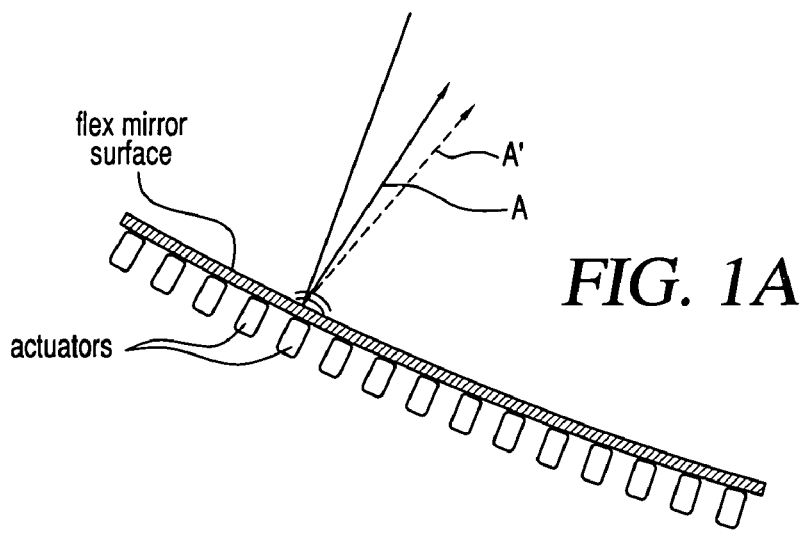
FIG. 1A is conceptual view of AO (adaptive optics) as known in the art of deformable mirrors for astronomical telescopes with actuators at an exterior of the reflective mirror plane.
Figure 1B:
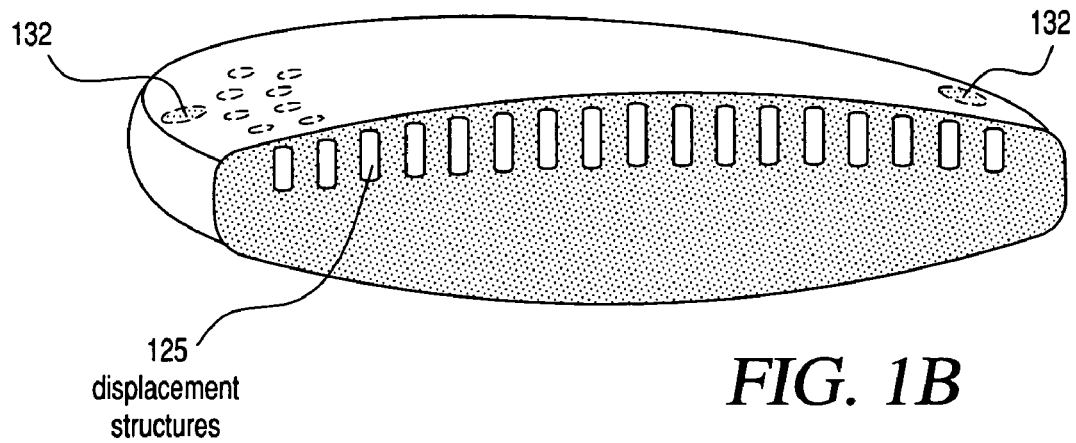
FIG. 1B is a conceptual representation of a lens element, for example and IOL or contact lens, including transparent index-matched soft polymer displacement structures or actuators at an interior plane of the lens in one embodiment of the AO (adaptive optics) structure corresponding to the invention.

I. Principles of Shape Memory in Polymers

Practically all embodiments of the invention utilize a shape memory polymer (SMP) to enable fluid displacement, fluid handling and in general actuation of the displacement structures of the adaptive optic according to the invention. For this reason, a background on shape memory polymers is provided. Some embodiments of the adaptive optic also utilize heat shrink polymers that are well known in the art, and it is not necessary to provide additional background on such polymers. Collectively, the shape memory polymers and heat shrink polymers are referred to herein as shape-change polymers.

Shape memory polymers demonstrate the phenomena of shape memory based on fabricating a segregated linear block co-polymer, typically of a hard segment and a soft segment. The shape memory polymer generally is characterized as defining phases that result from glass transition temperatures in the hard and a soft segments. The hard segment of SMP typically is crystalline with a defined melting point, and the soft segment is typically amorphous, with another defined transition temperature. In some embodiments, these characteristics may be reversed together with the segment's glass transition temperatures.

In one embodiment, when the SMP material is elevated in temperature above the melting point or glass transition temperature $T_g$ of the hard segment, the material then can be formed into a memory shape. The selected shape is memorized by cooling the SMP below the melting point or glass transition temperature of the hard segment. When the shaped SMP is cooled below the melting point or glass transition temperature of the soft segment while the shape is deformed, that temporary shape is fixed. The original shape is recovered by heating the material above the melting point or glass transition temperature of the soft segment but below the melting point or glass transition temperature of the hard segment. (Other methods for setting temporary and memory shapes are known which are described in the literature below). The recovery of the original memory shape is thus induced by an increase in temperature, and is termed the thermal shape memory effect of the polymer. The temperature can be body temperature or another selected temperature above 37° C. for the present invention.

Besides utilizing the thermal shape memory effect of the polymer, the memorized physical properties of the SMP can be controlled by its change in temperature or stress, particularly in ranges of the melting point or glass transition temperature of the soft segment of the polymer, e.g., the elastic modulus, hardness, flexibility, permeability and index of refraction. The scope of the invention of using SMPs in IOLs extends to the control of such physical properties.

Examples of polymers that have been utilized in hard and soft segments of SMPs include polyurethanes, polynorborenes, styrene-butadiene co-polymers, cross-linked polyethylenes, cross-linked polycyclooctenes, polyethers, polyacrylates, polyamides, polysiloxanes, polyether amides, polyether esters, and urethane-butadiene co-polymers and others identified in the following patents and publications: U.S. Pat. No. 5,145,935 to Hayashi; U.S. Pat. No. 5,506,300 to Ward et al.; U.S. Pat. No. 5,665,822 to Bitler et al.; and U.S. Pat. No. 6,388,043 to Langer et al. (all of which are incorporated herein by reference); Mather, *Strain Recovery in POSS Hybrid Thermoplastics*, Polymer 2000, 41(1), 528; Mather et al., *Shape Memory and Nanostructure in Poly (Norbonyl-POSS) Copolymers*, Polym. Int. 49, 453-57 (2000); Lui et al., *Thermomechanical Characterization of a Tailored Series of Shape Memory Polymers*, J. App. Med. Plastics, Fall 2002; Gorden, *Applications of Shape Memory Polyurethanes*, Proceedings of the First International Conference on Shape Memory and Superelastic Technologies, SMST International Committee, pp. 120-19 (1994); Kim, et al., *Polyurethanes having shape memory effect*, Polymer 37(26):5781-93 (1996); Li et al., *Crystallinity and morphology of segmented polyurethanes with different soft-segment length*, J. Applied Polymer 62:631-38 (1996); Takahashi et al., *Structure and properties of shape-memory polyurethane block copolymers*, J. Applied Polymer Science 60:1061-69 (1996); Tobushi H., et al., *Thermomechanical properties of shape memory polymers of polyurethane series and their applications*, J. Physique IV (Colloque C1) 6:377-84 (1996).

The scope of the invention extends to the use of SMP foams for use in elastic composite structures, wherein the capsular shaping element utilizes the polymer foam together with an expanse of nickel titanium alloy. See Watt A. M., et al., *Thermomechanical Properties of a Shape Memory Polymer Foam*, available from Jet Propulsion Laboratories, 4800 Oak Grove Drive, Pasadena, Calif. 91109 (incorporated herein by reference). SMP foams function in a similar manner as the shape memory polymers described above. The scope of the invention also extends to the use of shape memory polymers that are sometimes called two-way shape memory polymers that can moved between two predetermined memory shapes in response to varied stimuli, as described in U.S. Pat. No. 6,388,043 to Langer et al. (incorporated herein by reference).

Shape memory polymers foams within the scope of the invention typically are polyurethane-based thermoplastics that can be engineered with a wide range of glass transition temperatures. These SMP foams possess several potential advantages for intraocular implants, for example: very large shape recovery strains are achievable, e.g., a substantially large reversible reduction of the Young's Modulus in the material's rubbery state; the material's ability to undergo reversible inelastic strains of greater than 10%, and preferably greater that 20% (and up to about 200%-400%); shape recovery can be designed at a selected temperature between about 30° C. and 45° C. which may be useful for the implants; and injection molding is possible thus allowing complex shapes.

As described above, these polymers also demonstrate unique properties in terms of capacity to alter the material's water or fluid permeability, thermal expansivity, and index of refraction. However, the material's reversible inelastic strain capabilities leads to its most important property—the shape memory effect. If the polymer is strained into a new shape at a high temperature (above the glass transition temperature $T_g$) and then cooled it becomes fixed into the new temporary shape. The initial memory shape can be recovered by reheating the foam above its $T_g$.

II. Exemplary Ophthalmic Lenses Using Transparent Interior Displacement Structures 1. Type "A" Adaptive Optic System.

The adaptive optic system of the invention can be used in any type of lens, such as an IOL (intraocular lens), a contact lens or a corneal inlay to allow for post-fabrication power adjustment or post-implant adjustment. For purposes of explanation, the principles of the invention are first described with reference to an intraocular lens 10A for cataract treatment (FIG. 2A) adapted for in-the-capsule implantation. The three-piece IOL of FIG. 2A is shown with lenticular (lens) body 105 having haptics arms 106a and 106b as are known in the art for lens centration in an enucleated lens capsule.

Figure 2A:
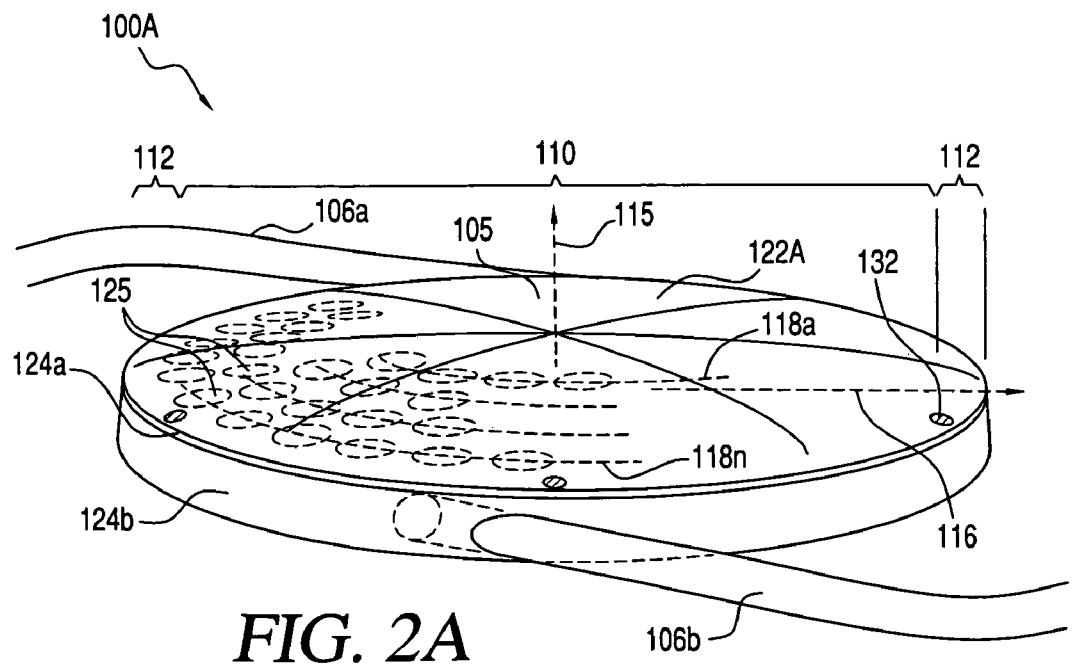
FIG. 2A is a perspective view of a Type "A" adaptive intraocular lens (IOL) with an interior phase carrying AO (adaptive optics) displacement structures.

In FIG. 2A, the IOL 100A has a lens body that defines a central optic portion 110 and peripheral non-optic portion 112 that is typically not designed for refraction, and may be transparent or non-transparent. The lens body 105 defines an optical axis indicated at 115 and transverse axis 116 that is perpendicular to the optical axis. The lens typically ranges from about 5.0 mm to 6.5 mm in diameter (not limiting) for an in-the-capsule IOL with different diameters for inlays (e.g., 3.0 to 6.0 mm.), anterior or posterior chamber lenses or contact lenses.

Figure 2B:
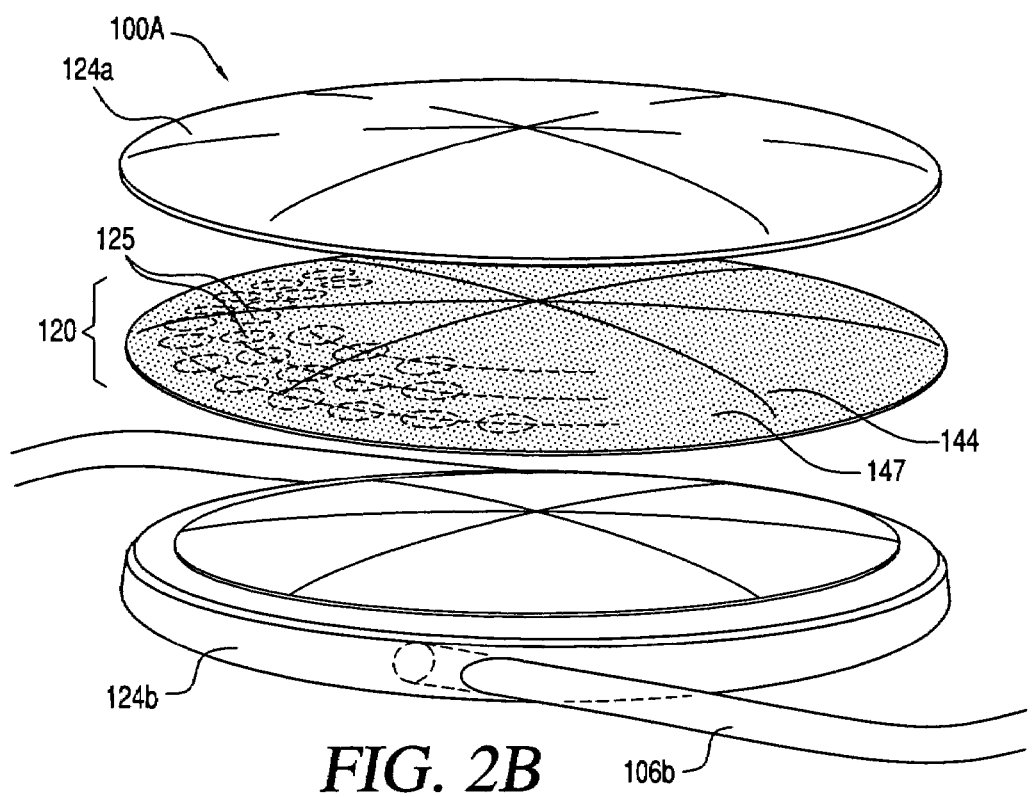
FIG. 2B is an exploded view of the components of the Type "A" adaptive optic of FIG. 2A showing the interior phase carrying the AO displacement structures corresponding to the invention.

As can be seen in FIG. 2A and the exploded view of FIG. 2B, the IOL includes an interior phase or layer 120 of the lens between the anterior and posterior lenticular surfaces indicated at 122A and 122B. The interior phase 120 comprises a novel transparent adaptive layer that is designed to controllably flex at least an anterior thin flexible surface layer indicated at 124a (FIG. 2B). In the embodiment of FIG. 2B, the complete lens is shown in exploded view with the interior phase 120 assembled between the (first) anterior body layer 124a and the (second) posterior body portion or layer 124b, with both layers being substantially fluid impermeable transparent polymers with any suitable refractive index as is known in the art. It should be appreciated that the lens can any shape, such as bi-convex, plano-convex, plano-concave, convexo-concave or comprise a thin diffraction element.

More specifically, the lens interior phase 120 defines a plurality of spaces 125 or volumes that carry a volume of a selected media M that functions as a displacement structure for applying forces to displace and deform the thin flexible surface layer 124a to locally modify lens curvature overlying the space 125. The terms spaces, displacement structures and force-applying structures are used interchangeably herein, identified by reference number 125, to describe the spaced apart adaptive structures that enable the adaptive optic and which are designed to actuate and deform and modify the shape of the surface layer 124a.

As can be seen in FIGS. 2A and 2B, the interior phase 120 defines pattern of spaces or displacement structures 125 (collectively) in a spaced-apart fixed arrangement. Each displacement structure 125 comprises a volume of selected media M that is alterable in a volume parameter or other physical property to modify the local shape of the lenticular surface 122A. The structures 125 are at time referred to as force-application structures herein since each such structure 125, or any collective number of actuatable structures, are capable of deforming the lens surface 124a by application of forces as each structure 125 is altered from a first stable volume or shape to a second expanded volume or shape. Of particular interest, the displacement structures 125 define a selected micro-scale that makes the system suitable for correcting higher order aberrations. The displacement structures 125 also can be actuated globally to alter the spherical power of lens.

In the interior phase 120, each displacement structures 125 in the embodiment of FIGS. 2A and 2B is of a polymeric media that has an index of refraction that matches body portions or layers 124a and 124b. The lens according to the invention has in total from about 10 to 1000 displacement structures 125. More preferably, the lens has from about 20 to 200 such displacement structures 125 in a fixed pattern that are suited to correct higher order wavefront aberrations.

The structures 125 also can be designed with similar or different dimensions, volumes and amplitudes of adjustment for different strategies in post-implant correction of the lens. Typically, the displacement structures 125 are arranged in a pattern that defines concentric circles 128a-128n about the optical axis 115. The number of concentric circles 128a-128n can range from 1 to about 500. More preferably, the concentric circles 128a-128n range from about 2 to 50.

The scope of the invention includes any adaptive optic for vision correction or other purposes that comprises a lens body formed with a plurality of microfabricated spaces 125 that carry media volumes of less than 1000 nanoliters therein. The lens body further defines flexible surface layer 124a defining a surface region 140 overlying each space that is deformable toward or away from each said space when the media therein is actuated. By the term actuated, it is meant that the media is altered in volume, porosity, hydrophilicity or pressure.

The displacement structures 125 are disposed in a fixed pattern, are index-matched and are adapted to apply deforming forces to the flexible surface for lens power modification. The displacement structures 125 are provided in a scale and number suitable for the correction of predominant aberrations, defocus and spherical aberration, as well as higher order aberrations.

In one exemplary lens 10A, shown in FIGS. 2A and 2B, the displacement structures 125 are of a transparent photomodifiable polymer or a shape memory polymer in the classes described above. The shape memory polymer is of a type suited for the AO layer that actuates by expanding its shape envelope to thereby apply displacement forces. In this embodiment, each displacement structure itself is targetable with a laser beam to adjust its dimension or envelope to thereby apply forces to a local portion of anterior surface 122A to modify its shape. More detailed illustrations of the displacement structures 125 of FIGS. 2A and 2B, the method of making lens 100A and the method of use of lens 100A are provided in FIGS. 3A-3B, 5, 7, 8A-8B and 9A-9B below.

FIGS. 3A-3L illustrate the principles of the adaptive displacement structures corresponding to the invention, wherein each displacement structure 145A-145F carries at least one shape change polymer that is photomodifiable by thermal, chemical or other effects to cause fluid displacement in one of a number of manners. All such displacements of fluids are designed to directly or indirectly apply deforming pressures to a local portion or a flexible, adaptive lens surface layer. The use of a displaceable fluid layer 144 (see FIG. 2B, 3A-3B and 6A) to apply pressure to a flexible lens surface is advantageous since it results in smooth radii of curvature of the actuated lens surface for better correction of higher order aberrations that may require a plurality of local deformations.

Figure 3A:
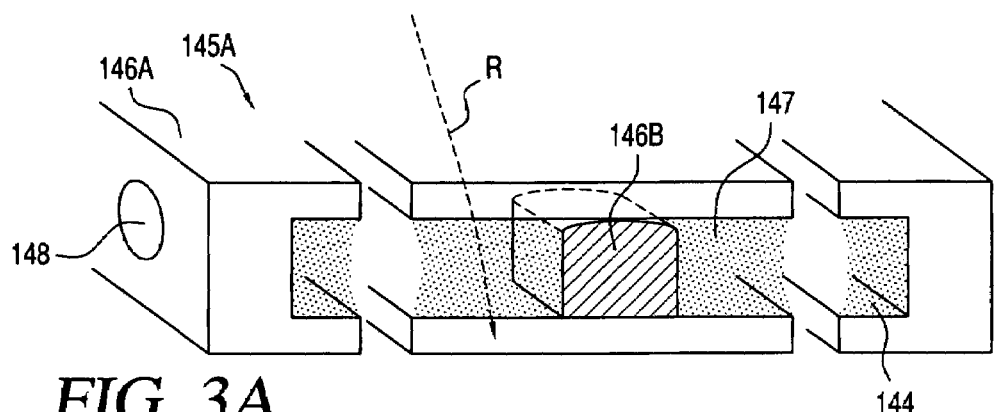
FIGS. 3A-3B are schematic illustrations of a first type of polymer monolith that functions as a displacement structure and its method of fabrication in an isovolumetric refractive device.
Figure 3B:
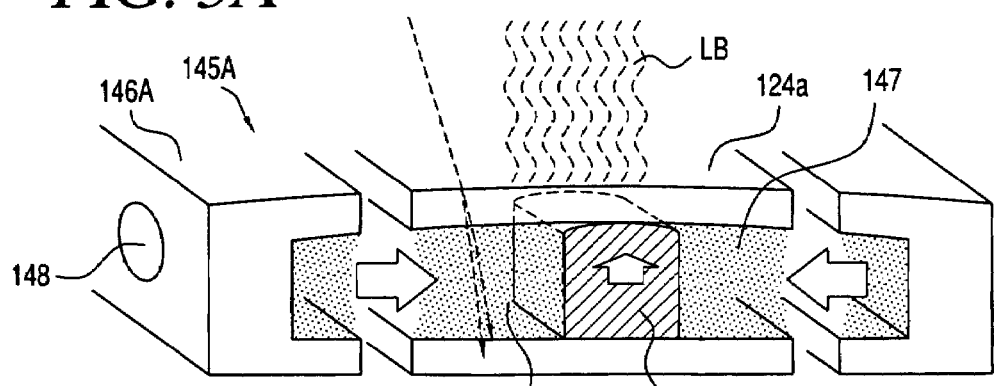

In FIGS. 3A-3B, the single displacement structure 145A can be considered a cartoon of a refractive structure. A first polymer monolith 146A is of a flexible polymer known in the art of IOLs and the second polymer monolith is a shape memory polymer 146B in its first temporary shape in FIG. 3A. FIG. 3A shows an incident light ray R and its refraction. The combined polymer monolith or structure 145A defines an interior fluid-filled space 147 that actuates the adaptive optic by providing a fluid 144 that interfaces with, supports and applies a displacement force against a flexible lens surface 124a that extends laterally between two lateral support regions to provide the lens surface with selected shape or curvature.

Of particular interest, the displacement structure 145A is an isovolumetric refractive structure wherein the net volume of the fluid and the first polymer monolith remains unchanged, but wherein actuation of the second shape memory polymer monolith 146B, in this case in a vertical direction in FIG. 3A by photothermal effects from light beam LB, causes redistribution of fluid pressure in fluid media 144 indicated by the arrows so that the fluid supports the laterally extending portions of surface layer 124a thereof. The first polymer monolith can optionally have a flex-wall portion 148 outside the refractive portion of the displacement structure to accommodate some changes in fluid pressure. As can be seen if FIG. 3B, the light ray R is indicated with its modified refraction.

Figure 3C:
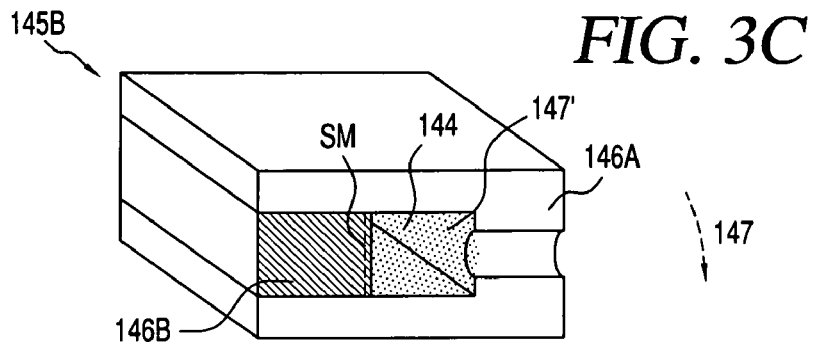
FIGS. 3C-3D are schematic illustrations of a second type of polymer monolith that functions as a displacement structure and its method of fabrication.
Figure 3D:
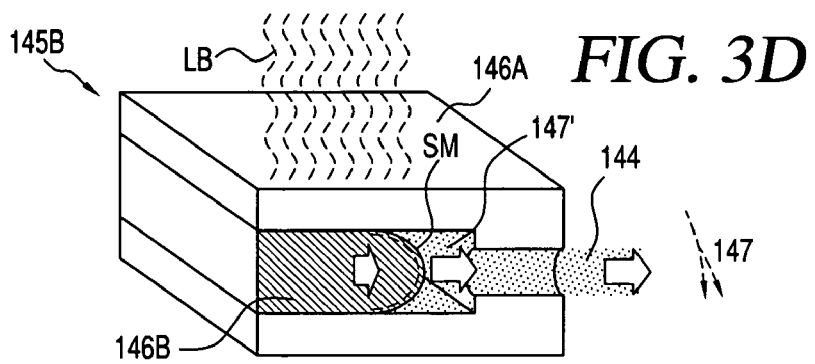

In FIGS. 3C-3D, another exemplary displacement structure 145B is similar to that of FIGS. 3A-3B except that the first polymer monolith 146A and the second shape memory polymer monolith 146B are assembled to displace fluid 144 to the first space portion 147 as in FIG. 3B that actuates the adaptive optic and flexible lens surface 124a with fluid 144 displaced from lateral space portion 147'. In other words, the shape memory polymer monolith 146B functions as a displacement means or pump means to displace fluid 144 to deform the flex surface over the interior space indicated at 147 (cf. FIG. 3B). The polymer 146B is altered by photothermal effects as described above.

In FIGS. 3C-3D, the shape memory polymer 146B is shown as having a surface modification SM, which indicates that the polymer has a modified surface that is substantially fluid impermeable to better displace the fluid. In some SMPs, the expansion of the polymer is a selected direction may require an in-fill media to fill open pores in the polymer if an open cell SMP is used, in which case the polymer would be provided with a fluid media source internal or external to the implant (not shown) as can be easily understood to facilitate the expansion of the polymer. This displacement structure 145B of FIGS. 3C-3D thus can incrementally and irreversibly displace fluid 144, and is used in several embodiments lens to actuate the adaptive optic, and is described in more detail below.

Figure 3E:
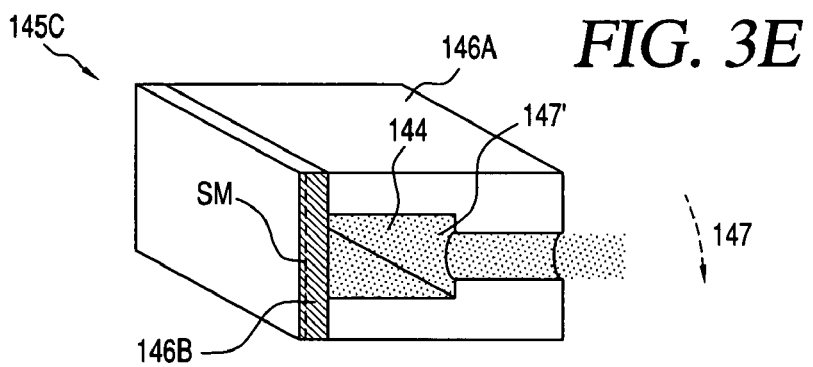
FIGS. 3E-3F are schematic illustrations of a third type of polymer monolith that functions as a displacement structure and its method of fabrication.
Figure 3F:
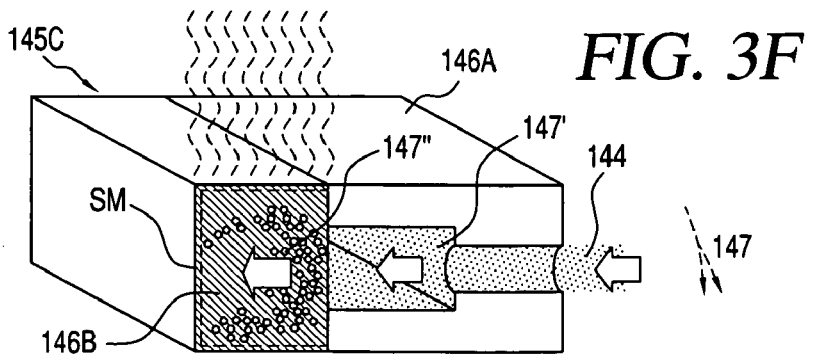

FIGS. 3E-3F illustrate another exemplary displacement structure 145C that functions in opposite manner of the structure of FIGS. 3C-3D. As can be seen in FIG. 3E, the assembly again is of a first polymer monolith 146A (a non-shape change polymer) and the second shape memory polymer monolith 146B that are assembled to displace fluid 144 from the first fluid-filled space portion 147 (as in FIG. 3B) that actuates the lens surface 124a to the lateral space portion 147' within the displacement structure 145C. In this embodiment, the shape memory polymer 146B functions as a sponge-like displacement means to draw fluid 144 into its interior spaces indicated at 147" as it moves from its temporary compacted shape (FIG. 3E) to its expanded memory shape (FIG. 3F).

To accomplish this task, an open-cell permeable shape memory polymer foam or CHEM is utilized which can expand to cause a potential interior space to expand to an actual interior space 147" and suction fluid 144 therein. In this embodiment, the fluid impermeable surface modification SM is provided about an exterior of the displacement structure 145C. When used in an adaptive optic, the displacement structure 145C is disposed about a periphery of the lens to provide a region for the SMP monolith 146B to expand so as not to affect the refractive parameters of the lens. The displacement structure 145C of FIGS. 3E-3F can incrementally and irreversibly displace fluid 144, and can be combined with the structure 145B of FIGS. 3C-3D to provide a reversible displacement system with a predetermined amount of amplitude.

Figure 3G:
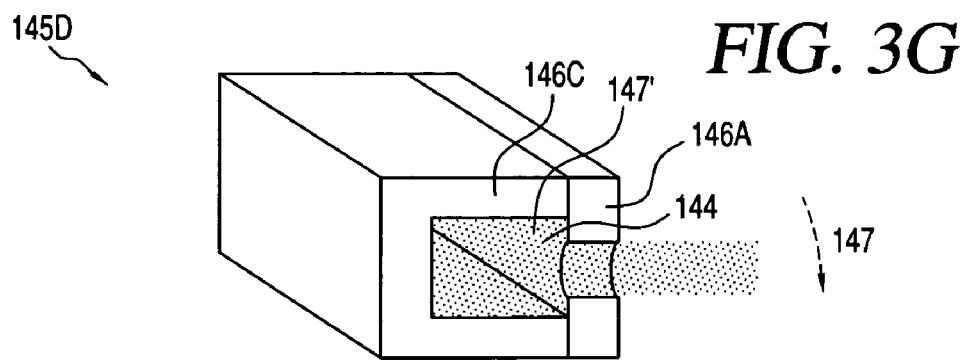
FIGS. 3G-3H are schematic illustrations of a fourth type of polymer monolith that functions as a displacement structure and its method of fabrication.
Figure 3H:
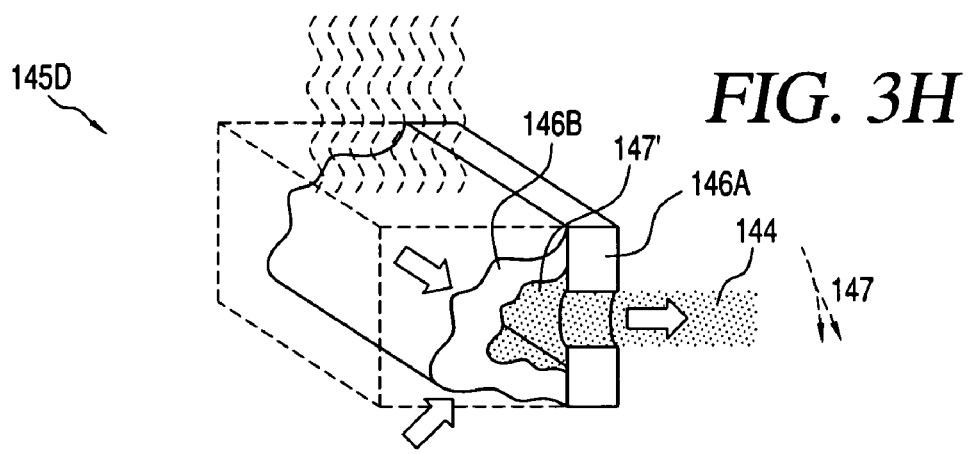

FIGS. 3G-3H illustrate another exemplary displacement structure 145D that functions as the structure 145B of FIGS. 3C-3D to displace fluid. In this embodiment, the structure again is of a first polymer monolith 146A (a non-shape change polymer) and the second shape change heat-shrink polymer monolith 146C that can displace fluid 144 to the first fluid-filled space portion 147 (as in FIG. 3B and 3D) to actuate the lens. In this case, the to the lateral space portion 147' within the displacement structure 145C. In this embodiment, the heat-shrink polymer monolith 146C displaces fluid 144 from the spaces portion indicated at 147' to the space 147 with the optic portion of the adaptive optic.

Figure 3I:
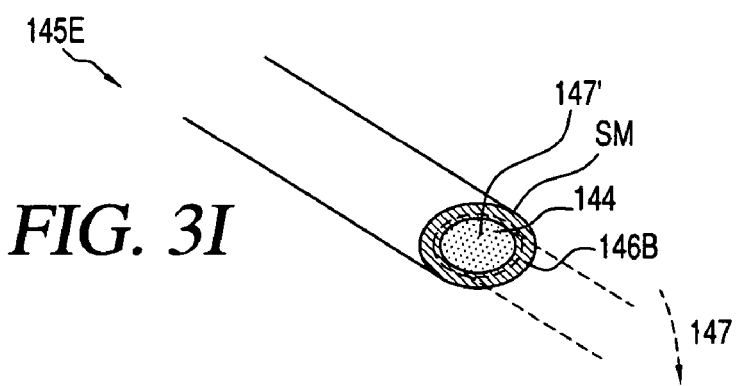
FIGS. 3I-3J are schematic illustrations of a fifth type of polymer monolith that functions as a displacement structure and its method of fabrication.
Figure 3J:
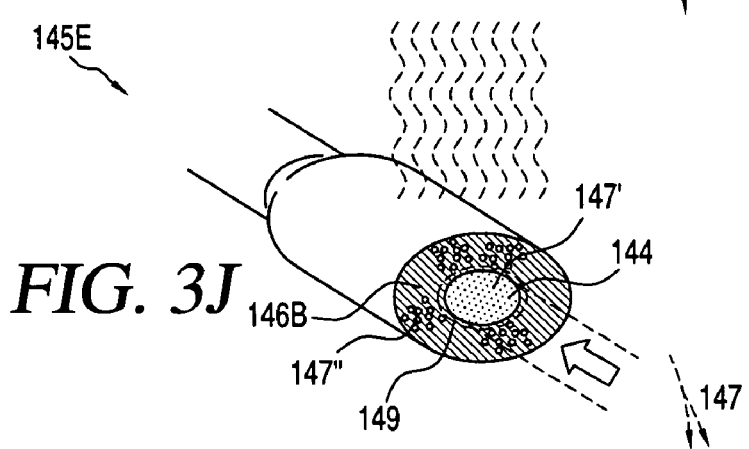

FIGS. 3I-3J illustrate another exemplary displacement structure 145E that functions as the structure 145C of FIGS. 3E-3F to displace fluid. This embodiment depicts that the polymer monolith 146D can be a co-polymer of a non-shape change polymer and second memory polymer, or a SMP monolith with a permeable non-collapsible layer 149 about the fluid-filled space portion 147' which communicates with space portion 147 (as in FIG. 3B and 3D) that actuate the adaptive optic.

In this case, the space portion 147' is simply defined as a lumen in a monolithic wall that is at least partly an open-cell permeable shape memory polymer foam or CHEM. As described above, the displacement structure can expand to cause a potential interior space to expand to an actual space indicated 147" and can suction fluid 144 therein from the adaptive optic space 147. It should be appreciated that a heat shrink polymer can also simply be a tubular structure adapted for photothermal shrinkage to pump fluid 144 to a space 147 in the optic portion of the adaptive optic.

Now turning to another exemplary adaptive optic lens 100B that utilizes one of the fluid displacement structures just described in FIGS. 3A-3J, FIG. 4 illustrates a lens with an interior phase 120 that has a plurality of displacement structures 125 that first each and second displacement structure portions 126a and 126b. The interior phase 120 again is a thin layer that is enveloped by the anterior lens surface 124a and the posterior lens body 124b, wherein an exploded view would be similar to FIG. 3. The displacement structures 125 comprise a photomodifiable thin film polymer 127 that envelops a flowable media that comprises the second structure portion 126b.

In this embodiment, the flowable polymer 126b can have a thermally stable property (as in a silicone) and the thin film 127 (first portion 126a) is of a polymer type that actuates by shrinking its shape envelope to thereby apply displacement forces-not to the lens surface 124a directly but to the enveloped flowable media therein. Thus, the shrinkage of thin-cross section portions 126a will displace the flowable media to actuate swell the axial height of the second displacement structure portion 126a. An enlarged view of the actuation of an exemplary schematic is provided below in FIG. 3H, and this introduction is for the purpose of explaining that the shape change polymers of the invention encompass SMP types that are expandable in envelope to comprise an actuator and those that are heat-shrink types of polymers that are shrinkable in envelope to comprise an actuator.

Figure 4:
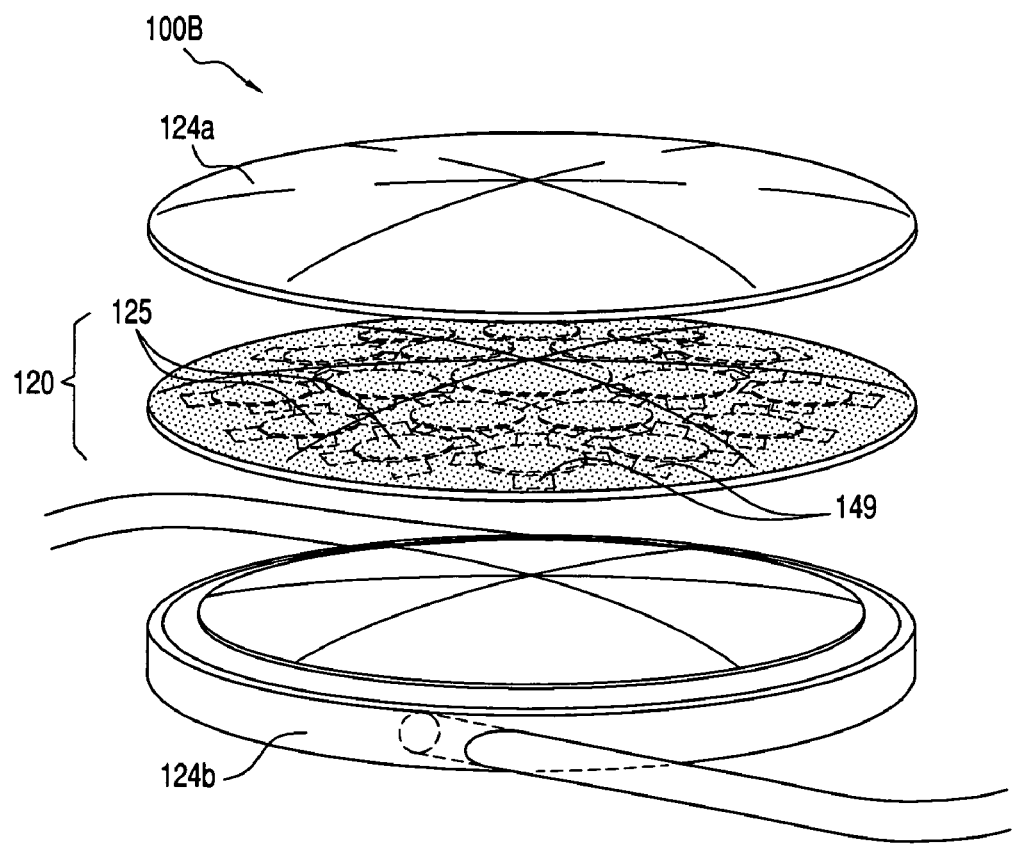
FIG. 4 is an exploded view of an alternative Type "A" adaptive optic showing the interior phase carrying the alternative displacement structures corresponding to the invention.
Figure 5A:
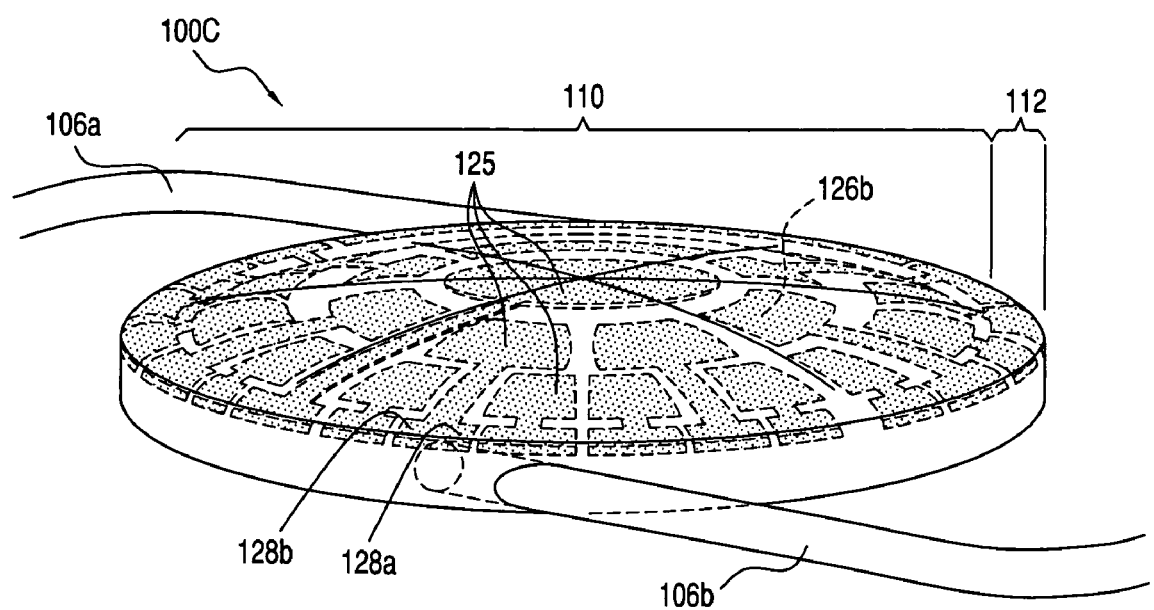
FIG. 5A is a perspective view of another alternative Type "A" adaptive optic showing the interior phase carrying the alternative displacement structures.

In another exemplary lens 100C as shown in FIGS. 5A, the interior phase 120 again has a plurality of displacement structures 125 with first and second photomodifiable polymers 128a, 128b that are coupled to the encapsulated flowable media 126b as described in the previous lens 100B of FIG. 4. The interior phase 120 again is a thin layer that is enveloped by the anterior lens surface 124a and the posterior lens body 124b, with an exploded view in FIG. 5B.

Of particular interest, the first and second photomodifiable polymers 128a and 128b are of both the types of polymers used in the lenses 100A and 110B. The first photomodifiable polymer 128a is an SMP type that is expandable in envelope and the second photomodifiable polymers 128b is a heat-shrink type of polymers that is shrinkable in envelope. The combination of opposing shape effects in polymers is utilized to provide displacement structures 125 that can actuate in two directions for a certain number of cycles.

Figure 5B:
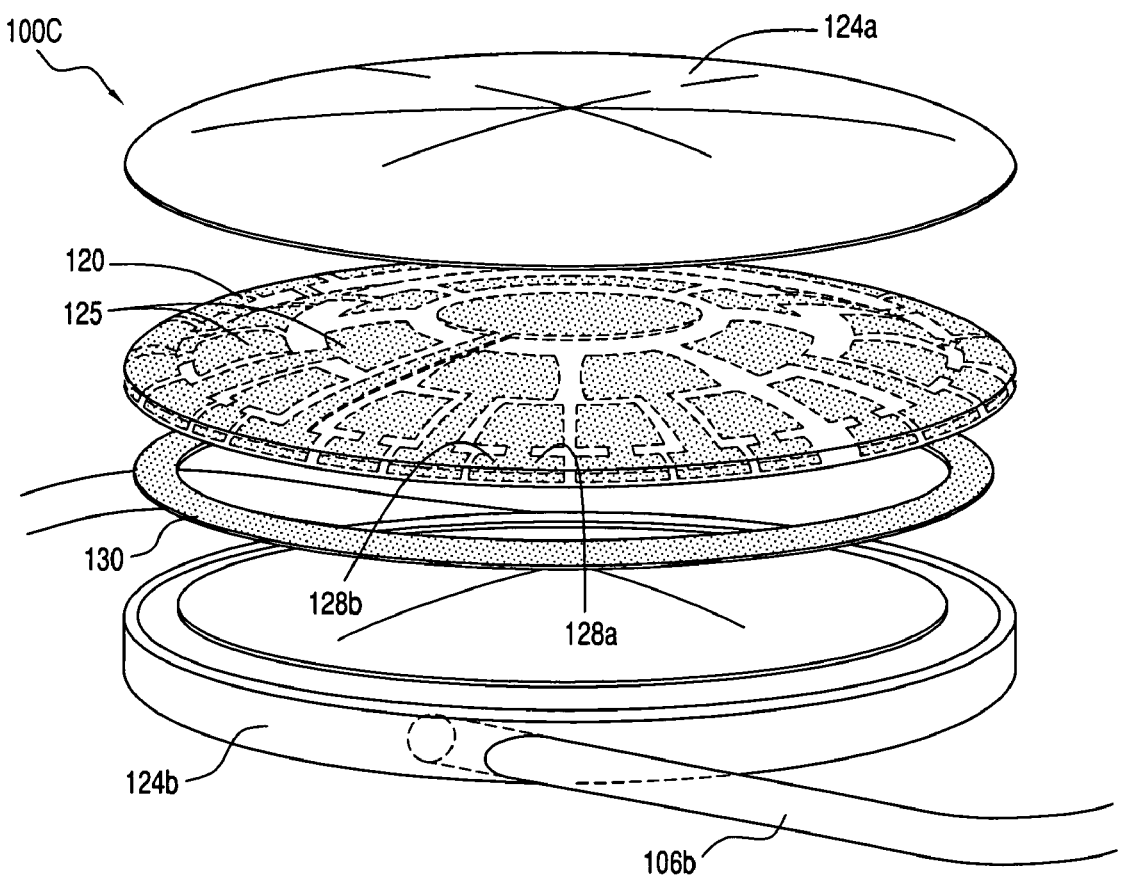
FIG. 5B is an exploded view of adaptive optic of FIG. 5A showing its interior phase and a non-transmissive peripheral element.

In the exemplary embodiment of FIGS. 5A-5B, the first and second photomodifiable polymers 128a and 128b of each displacement structure 125 are disposed in the periphery of the lens and are adapted to change volume (or other parameter) to apply or reduce pressure on the flowable media 126b which, in turn, applies forces to a local region of anterior surface 122A to modify its shape. The lens 100C of FIGS. 5A-5B allows for modification of lens shape exactly as lenses 100A and 100B of FIGS. 2 and 4, except that the light energy can be targeted at the periphery or non-optic portion 112 of the lens. This is advantageous for certain photo-modifiable polymers that are adjusted with energy densities that could pose even a slight risk of damage to the retina. By positioning the photo-modifiable polymers in the non-optic portion 112 of the lens, a non-transmissive composition or backing can be provided as indicated at 130 in FIG. 4 to prevent any laser beam from irradiating the patient's retina. More detailed illustrations of the lens 100C and its displacement structures 125 as in FIGS. 5A-5B, its method of use and method of making are provided in FIGS. 11A-11D.

The scope of the invention includes the use of any displacement photomodifiable media in or coupled to spaces 125 that can be actuated to controllably alter a physical or chemical parameter thereof to displace and deform a lens surface region over each space 125. The photomodifiable media can be a shape-change polymer, a polymer media that changes density or porosity in a fluid environment, any displaceable media such as a fluid or gel that is moved or pressurized, any combinations thereof.

In other words, each displacement structure 125 comprises media or a combination of media that is adjustable from a first stable functional parameter to a second stable parameter in response to energy applied to locations on the lens body to individually alter each displacement structures 125, the functional parameters being in the class consisting of media volume, media shape, media porosity, media density and media internal pressure. As will be described below, the preferred method of applying energy to the lens body is the use of a laser or a non-coherent directed light energy beam.

In FIG. 2, it can be seen that the anterior surface 122A of the lens carries reference markers 132 about its periphery which may be provided in any suitable number, for example from 1 to 10. The reference marks 132 are utilized to allow a light source and its computer-controlled scanning system to localize a light beam on a targeted location in the lens 100A. The reference marks 132 typically function based on reflectivity with a reference light beam and sensing system similar to that used in a CD (compact disc), which is known in the art and need not be described further herein.

2. Methods of Making and Using Interior Lens Phase of Type "A" Adaptive Optic System.

The scope of the method of making the adaptive optic corresponding to the invention, in general, covers the field of creating patterned adaptive features in an interior lens phase of an IOL or other vision correction lens or providing spaces 125 filled with a media by use of precision microjet dispensing of media droplets on a lens component in a data-driven manner. Various terms are applied to such accelerated fluid droplet dispensing onto a targeted location on a substrate, and the terms microjet dispensing and drop-on dispensing will be used alternatively herein. The drop-on system also is used to fill features microfabricated into lens components.

Such drop-on dispensing is novel and advantageous in adaptive optic fabrication since very small precise polymeric fluid volumes must be controllably placed on or within a lens component. As a non-contact fluid dispensing process, the volumetric accuracy is not affected by how the fluid polymeric media wets the substrate as may be the case wherein positive displacement or pin transfer systems "touch off" a fluid onto a substrate as it is dispensed. An additional advantage is that the jetted fluids can be dispensed onto or into substrate features such as wells or other features that are provided to control wetting and spreading of the fluid.

Drop-on dispensing can controlled single drop volumes as low as 5 picoliters and as high as 5 nanoliters. Such precision fluid dispensing is capable of producing and placing "droplets" of polymeric fluids and fluids carrying nanoparticles, with micron-scale precision, with the individual drops ranging about 10-200 μm in diameter, at dispensing rates of 0-25,000 per second for single droplets in a drop-on-demand system (described below) and up to 1 MHz for droplets in a continuous-mode system (described below).

Of particular interest, the method allows for highly precise polymer depositions in a data-driven manner to create the pattern of displacement structures 125 in the interior phase 120 of any adaptive optic according to the invention. The method allows for polymer deposition at a low cost (no tooling or molding required) in a noncontact, flexible and data-driven manner without masks, screens or the like since the lens pattern and print information is created directly from CAD data stored digitally. Drop-on demand systems have been extensively investigated and developed (Matrix-Jet™ microdispensing) by MicroFab Technologies, Inc., 1104 Summit Ave., Ste. 110, Plano, Tex. 75074.

In general, the physics and methods of microjet dispensing systems can differ substantially, but each system variant provides a repeatable generation of small droplets of fluid media accelerated at a high velocity from a jet onto a substrate. Two broad categories of fluid dispensing technologies for use in manufacturing are known: (i) drop-on-demand or demand mode systems, and (ii) continuous mode charge-and-deflect systems. These technologies are familiar to most people in the form of desktop ink-jet printers.

In a drop-on-demand fluid dispensing system, the fluid is maintained at ambient pressure and a transducer is utilized to create a droplet on demand. The transducer creates a volumetric change in the fluid to create pressure waves that travels to a jet or orifice wherein the pressure is converted to fluid velocity-which results in a droplet being ejected from the jet. The transducer in drop-on-demand systems can be piezoelectric material or a thin film resistor. In the later, the resistor causes a local fluid temperature to spike forming a vapor bubble which creates a volume displacement in the fluid media in a similar manner as the electromechanical action of a piezoelectric transducer.

In a "continuous mode" droplet dispensing system, a pressurized fluid is forced through an orifice, typically 25-80 μm in diameter, to form a liquid jet. Surface tension acts to amplify minute variations in the jet diameter causing the jet to break up into drops—a behavior normally referred to as Rayleigh breakup. If a single frequency disturbance in the correct frequency range is applied to the jetted fluid, the disturbance will be amplified and drops of extremely repeatable size and velocity can be generated at the applied disturbance frequency. Such a disturbance is generated by an electromechanical device (e.g., a piezoelectric element) that creates pressure oscillations in the fluid. This type of fluid dispensing is referred to as continuous-mode because droplets are continuously produced with their trajectories varied by electrostatic charges. To control the extremely uniform droplets generated by Rayleigh breakup, electrostatic forces are employed. The charged drops are directed to either the targeted location on a substrate or to a catcher by a fixed electrostatic field called the deflection field.

The drop-on-demand systems are much less complex than continuous-mode systems. On the other hand, demand mode droplet generation requires the transducer to deliver three or more orders of magnitude greater energy to produce a droplet, compared to continuous mode, which relies on a natural instability to amplify an initial disturbance. Either system can be used to accomplish the initial steps of fabricating the patterned interior phase 120 of the invention.

Figure 6A:
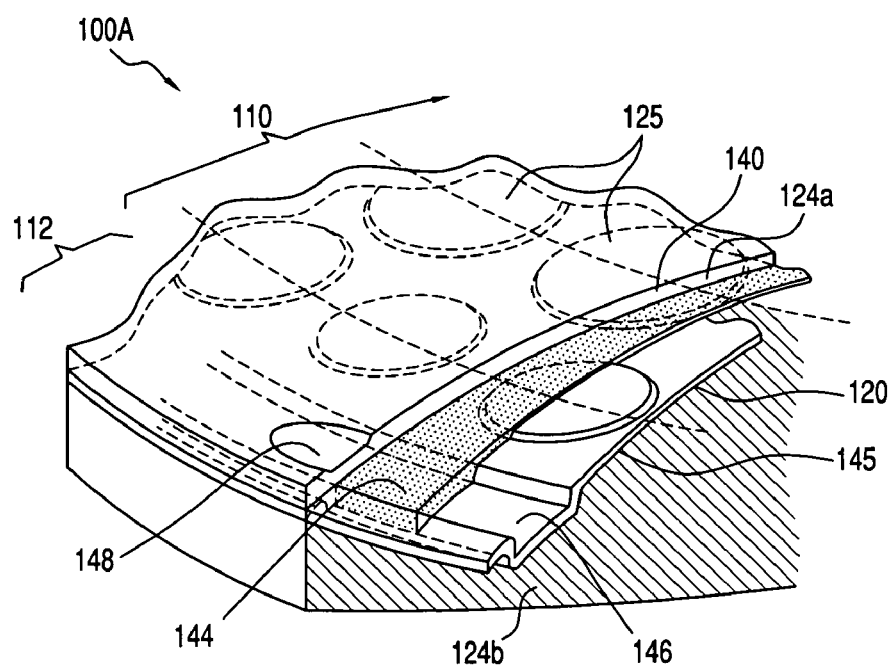
FIG. 6A is an enlarged cut-away view of a portion of the adaptive optic of FIGS. 2 and 3 showing its interior phase and features therein.

Now turning to FIG. 6A, an enlarged cut-away view of a portion of the first exemplary Type "A" lens 100A of FIGS. 2-3 is shown. The spaces or displacement structures 125 carry a polymeric media that comprises an index-matched photomodifiable shape memory polymer (SMP) as described above or in the literature identified above in Section I. The anterior lens layer 124a defines a selected thickness dimension A and modulus of elasticity (E) so that a surface region 140 of layer 124a (indicated with crosshatching) cooperates with the surface area of space 125 to insure that the radius of curvature in the deformed layer 124a is within selected parameters. The thickness dimension A of the deformable anterior layer 124a is from about 1 micron to 100 microns.

More preferably, the dimension A of anterior layer 124a is from about 5 microns to 50 microns. Still referring to FIG. 6A, the dimension B of the structure 125 across a principal transverse axis 116' thereof (cf. transverse axis 116 of lens body 105 in FIG. 2) is less than about 2000 μm (microns). More preferably, the transverse dimension A of the structure 125 is from about 100 microns to 500 microns, and the dimensions can vary with in each concentric pattern of displacement structures.

In FIG. 6A, it can be seen that the first and second polymer lens portions 124a and 124b envelope the interior phase 120 and an adjacent layer of flowable media indicated at 144. The intermediate flowable media 144 again is a thin layer of index-matched fluid, a very low modulus index-matched material, or an indexed-matched gel or porous structure with an index-matched fluid therein. In these exemplary embodiments, this intermediate media 144 is adapted to occupy a lens volume and provide stable refraction before and after adjustment lens with actuation of the displacement structures 125.

In the embodiments that utilize a fluid 144, a silicone of a selected viscosity can be used. Of particular interest for the invention, silicone fluids can be fabricated to provide the matching index of refraction as described above. Silicones change very little in viscosity over a wide temperature range, which together with their high wetting power can will provide the properties needed for the functioning of the adaptive structure of lens corresponding to the invention. Further, silicones fluids are inherently inert towards the other substrates that are anticipated to be used in the invention. All these characteristics, low viscosity change vs. temperature, dielectric stability, chemical inertness, shear stability, low surface tension, oxidative stability, thermal stability and high compressibility make silicone a logical candidate for use in the invention.

Further, it is believed that silicone fluids, in this application, will be found to be a biocompatible material for the interior of a lens implant following FDA regulatory reviews. The viscosity of silicones or other suitable fluids is typically measured in units called centistokes (cSt) wherein the lower the number, the thinner and less viscous the material. A fluid 144 for use in the lens can have a viscosity ranging from about 0.65 cSt to about 1,000,000 cSt, which ranges from a very low viscosity fluid upward to a high viscosity fluid. More preferably, the fluid 144 can have a fluid viscosity ranging from about 5.0 cSt to 100,000 cSt, which at the upper range resembles a slow moving gel. More preferably, fluid 144 can have a fluid viscosity ranging from about 10 cSt to 5,000 cSt.

A wide number of commercial sources of silicone fluids are known, for example, NuSil Silicone Technology, Inc. (www.nusil.com); General Electric, Inc. (www.gesilicones.com) and Dow Corning, Inc. (www.dowcorning.com). While silicone fluid is a preferred material for use in the invention, it should be appreciated that hydrogels and any other fluids fall with suitable matching indices, viscosities and biocompatibility fall within the scope of the invention.

In the lens 100A of FIG. 6A, each structure 125 is actuated to deform the surface portion 140 overlying the media by direct application and absorption of energy by the shape memory media that defines structure 125. The media can carry any suitable chromophore if required to absorb the selected wavelength. Each structure 125 is assigned an address. By the term address, it is meant that the spatial location of the lenticular surface overlying the adaptive element is assigned surface coordinates in relation to reference markers indicated at 130.

In the exemplary lens 100A of FIG. 6A, the interior phase 120 comprises a substrate 145 onto which the shape memory media is disposed, in a method described in more detail below. It can be seen that the peripheral portion 112 of the lens has an increased cross-section space 146 that carries a suitable volume of flowable media 144 that can migrate about the region between the flexible surface 124a and the actuatable interior phase 120 to fully occupy this space. The lens peripheral portion 112 overlying at least a portion of the increased cross-section space 146 also has a flex-wall portion indicated at 148 that can deform slightly to allow the migration of fluid 144 to or from the periphery after the displacement structures change in volume.

Figure 6B:
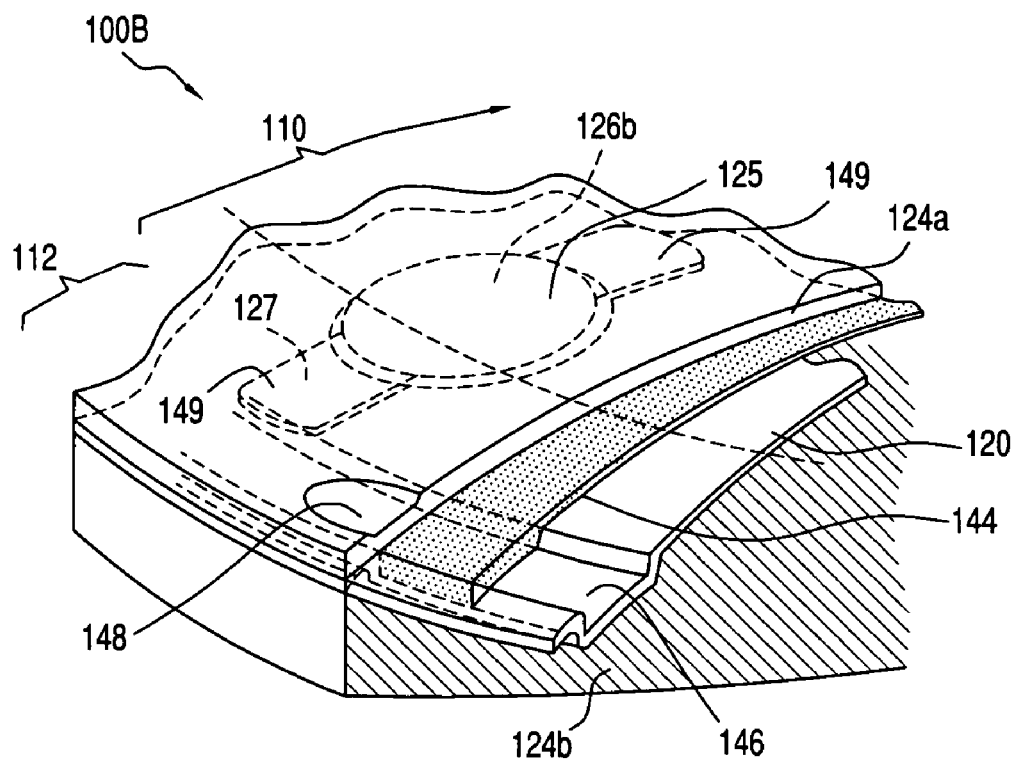
FIG. 6B is an enlarged cut-away view of the adaptive optic of FIG. 4 showing its interior phase and features therein.

Now turning to FIG. 6B, a portion of the second exemplary Type "A" lens 100B of FIG. 4 is shown in cut-away view. This lens 100B functions in a similar manner as that of FIG. 6A to deform the lens surface 124a, but as described above, utilizes a shape-change polymer that is of a heat shrink type. The displacement structure 125 thus comprises a first portion that is a photomodifiable thin film polymer 127 that envelops a flowable media or the second structure portion 126b. In this embodiment, the thin film 127 first portion is photo-actuated to heat-shrink its shape envelope to expel fluid from the thereby apply displacement forces to increase the axial height of the central portion of structure 125 to deform lens surface 124a by inflow of the flowable media 126b therein. In this embodiment, the heat-shrink shape envelope has at least one (or a plurality) of extending portions indicated at 149 (collectively). A plurality of extending portions 149 allow for independent targeting with light energy to allow for a controlled shrinkage of an extending portions 149 to actuate the lens. A more complete description will be provided below when explaining the method of making this interior phase 120.

Figure 6C:
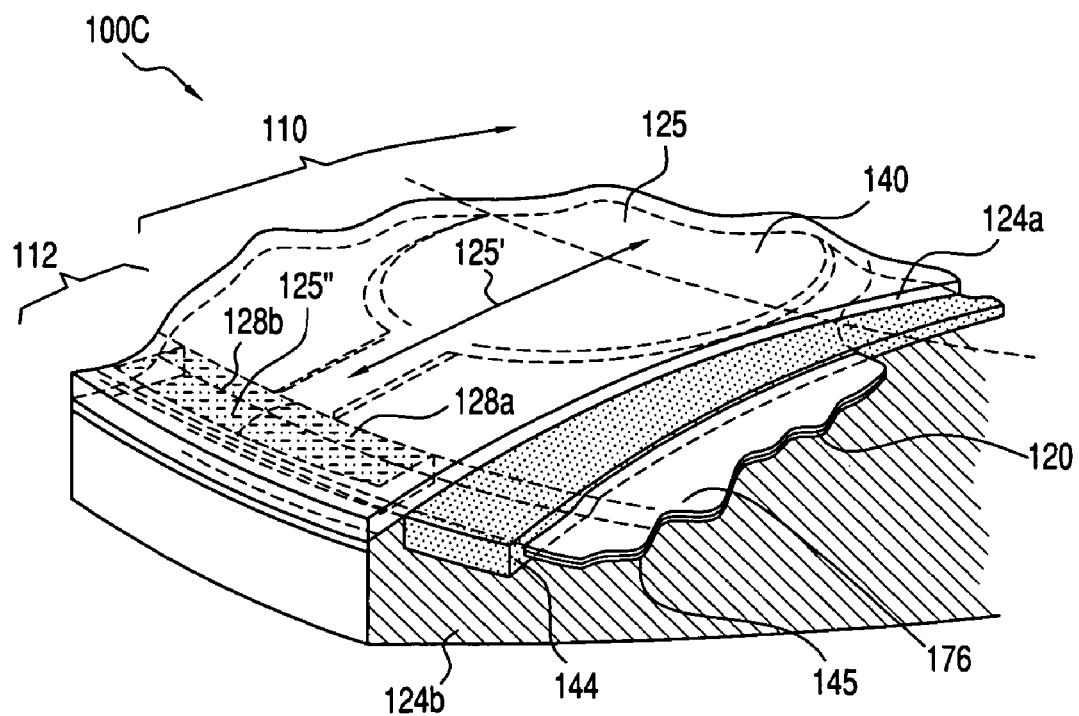
FIG. 6C is an enlarged cut-away view of the adaptive optic of FIGS. 5A-5B showing its interior phase and features therein.

Now turning to FIG. 6C, a portion of the third exemplary Type "A" lens 100C of FIGS. 5A-5B is shown in cut-away view. This lens 100C displaces the lens surface 124a in a manner similar to that of FIGS. 6A and 6B, except that (i) the photo-actuatable polymer media is disposed in the peripheral portion 112 of the lens body, and (ii) both heat expandable and heat-shrinkable polymers (128a and 128b, respectively) are integrated into the displacement structures 125 to allow reversible actuation. As discussed above and shown in FIG. 5B, this embodiment allows the use of higher fluences to actuate the shape-change media since the peripheral non-optic lens body 112 can carry a non transmissive composition 130 (see FIG. 5A) posterior of the targeted photomodifiable media.

In the lens 100C of FIG. 6C, the spaces or displacement structures 125 define a first space portion 125' and second space portion 125" that are carried again interior phase 120. In this embodiment, the interior phase 120 essentially floats within the flowable media layer 144. Peg structures (not shown) between members 124a and 124b though apertures in phase 120 can maintain the phase in a fixed location to prevent lateral migration.

The first space portion 125' of the displacement structure space is in the optic portion 110 of the lens and is adapted to change in volume and axial dimension to deform the overlying surface region 140 exactly as described in the text above accompanying FIG. 6A. The first space portion 125' carries the flowable media 126b that interfaces with first and second shape-change polymers 128a and 128b disposed in the second space portion 125" within the lens periphery 112.

It can be easily understood how the expansion or contraction of the first and second shape-change polymers 128a and 128b in the second space portion 125" can thereby cause fluid pressure and media flow to actuate the displacement structure. As can be seen in FIG. 6C, the shape change polymer and the flowable media 126b in first space portion 125' are sealably carried in the interior phase which has base substrate 145 and overlying cap layer 176 that can be fabricated in various manners as described below. All other aspects and dimensions of the lens components are similar in lens 100A, 100B and 100C of FIGS. 6A-6C.

Figure 7:
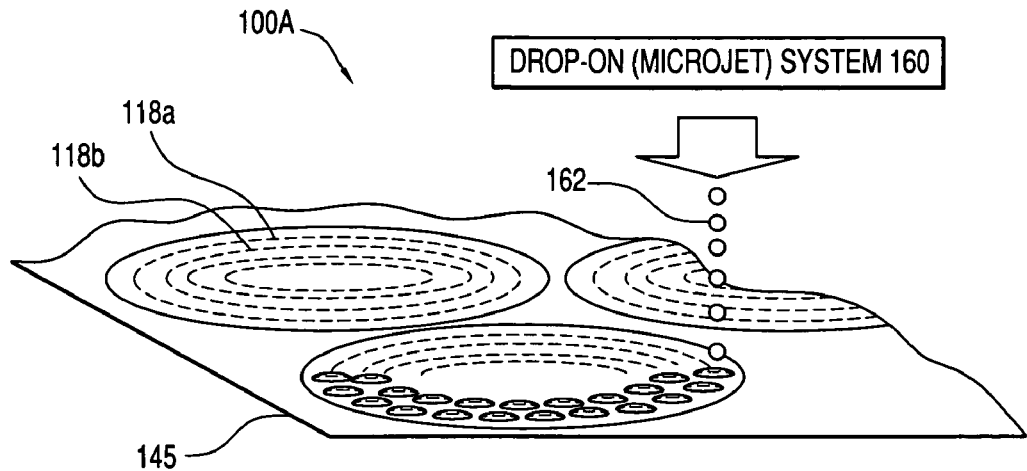
FIG. 7 is a perspective schematic view of an initial step in making an interior phase of a Type "A" adaptive optic as in FIG. 6A corresponding to a method of making the adaptive optic utilizing drop-on microjet fluid dispensing.
Figure 8A:
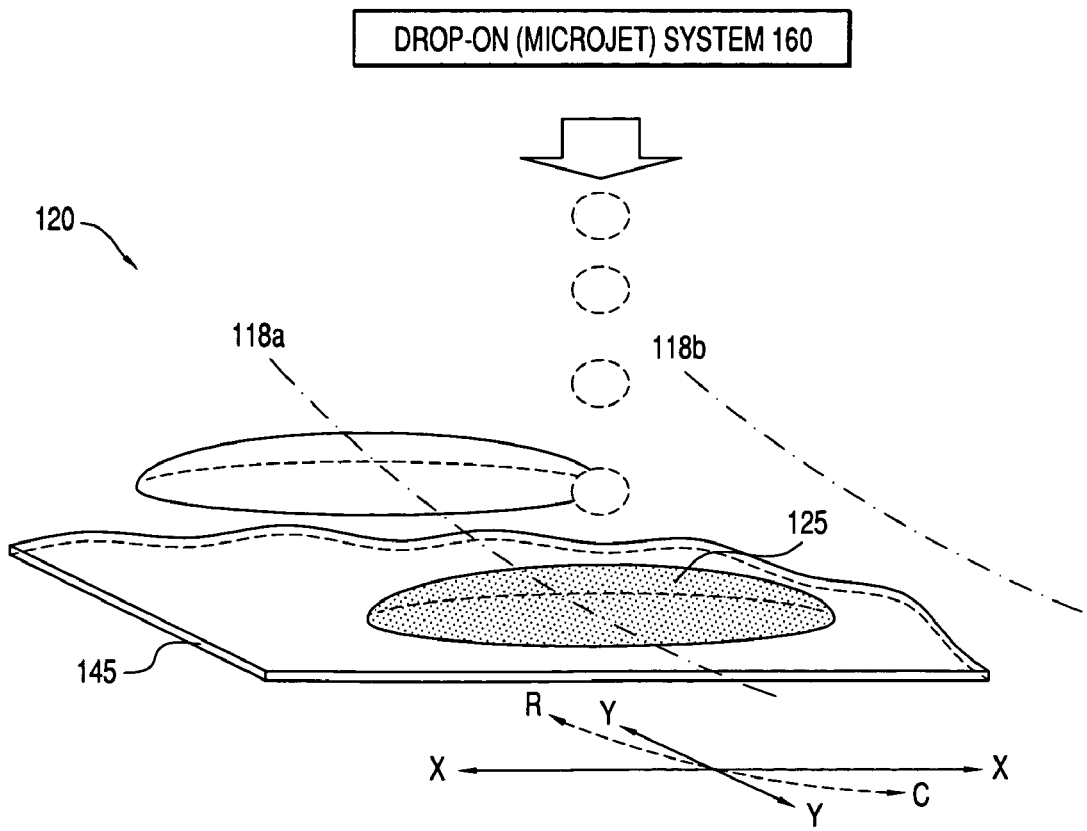
FIG. 8A is an enlarged perspective view of the initial step of making the interior phase and Type "A" displacement structures of FIG. 6A of a shape memory polymer (SMP)
Figure 8B:
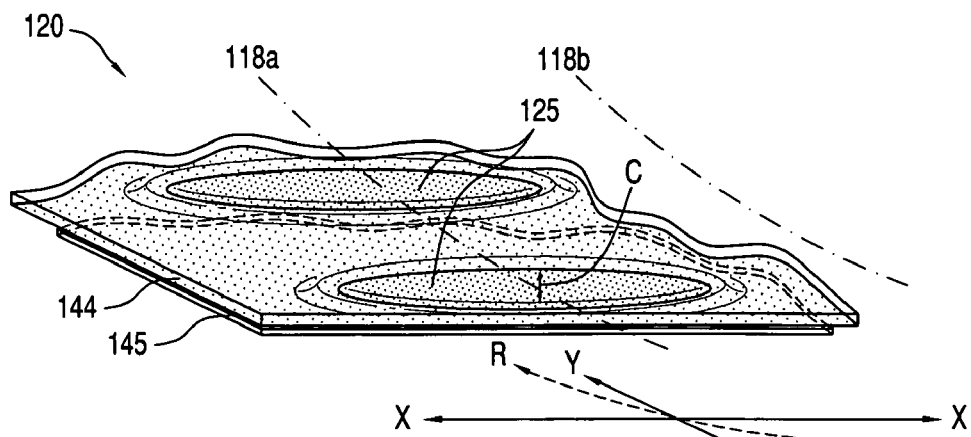
FIG. 8B illustrates following steps of the method of making the interior phase and displacement structures of FIG. 6A including altering the SMP to its compacted temporary shape and adding an interior fluid layer to the interior phase.

Now turning to FIGS. 7 and 8A-8B, the steps of making and using the interior lens phase 120 that is the core of the adaptive optic is shown schematically. In FIG. 7, the substrate 145 can comprise any very thin polymer film that is disposed on the stage of the drop-on microjet system 160 wherein a plurality of interior phase components can be fabricated contemporaneously, with each round substrate portion later cut from the film to make an interior phase 120.

In the fabrication of the interior phase 120 of the lens 100A of FIG. 5A, the drop-on system disposes a shape memory polymer media in a first state as described above to create the desired pattern in concentric circles 118a-118n. The droplets 162 can be used to create the displacement structures 125 in a desired volume ranging between about 100 picoliters and 1000 nanoliters.

FIG. 8A is a greatly enlarged view of two displacement structures 125 after being disposed on the substrate and polymerized or partially polymerized to define a memory shape with given axial height. FIG. 8B next illustrates the two displacement structures 125 of FIG. 8A after being compacted mechanically to second temporary state with an axial height C wherein a polymer segment of the SMP is polymerized to maintain the structure in its compacted state. The media can be shape memory polymer foam as described above. FIG. 8B also illustrates the fluid layer 144 disposed over the interior phase 120 by any suitable means such as drop-on dispensing or a similar spray-on system.

Fluid layer 144 also can comprise a thin gel layer or a photoscissable polymer that is provided in a gel or solid form and converted to a fluid by energy delivery after assembly of the lens components 120, 124a, 124b and 144. The interior phase 120 and displacement structures 125 of FIG. 8B are actuated by energy deliver by a beam from a light source, wherein the structure is returned toward its memory axial height.

Figure 9A:
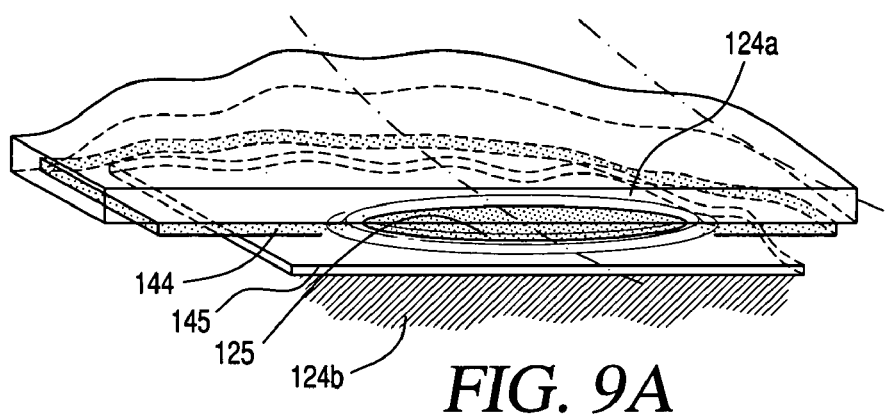
FIG. 9A illustrates the interior phase and displacement structure as is FIG. 8B assembled with a flexible anterior lens surface.
Figure 9B:
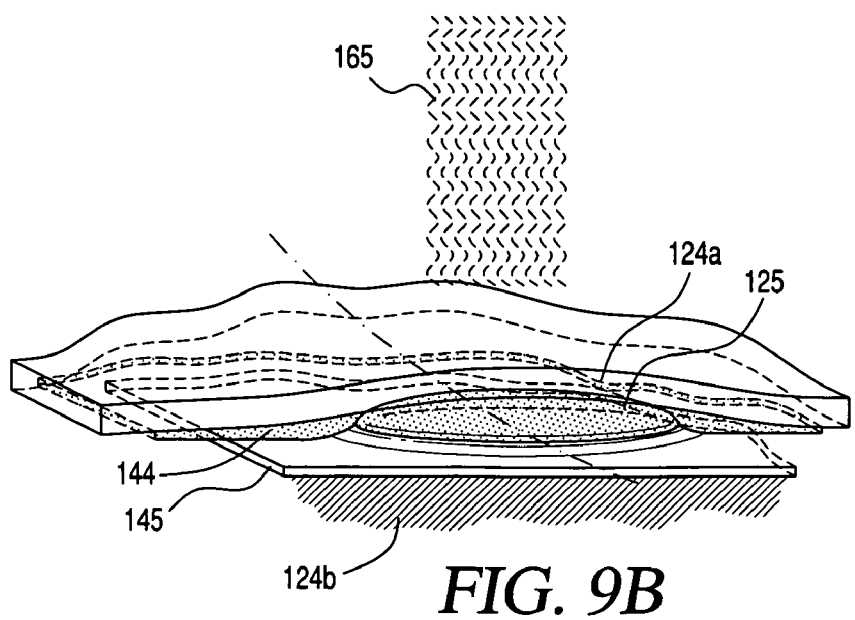
FIG. 9B illustrates the displacement structure as is FIG. 9A with the lens shape being modified in a wavefront aberration correction procedure.

FIGS. 9A and 9B show the actuation of the displacement structures 125 when assembled with the deformable lens surface 124a and base layer 124b to illustrate the shape change of region 140 overlying the structure 125. In FIG. 9B, it can be seen how fluid or gel layer 144 will migrate to occupy the entire space between the interior phase 120 and the deformable lens surface 124a to provide a continuous lens interior of index matched media.

Figure 10:
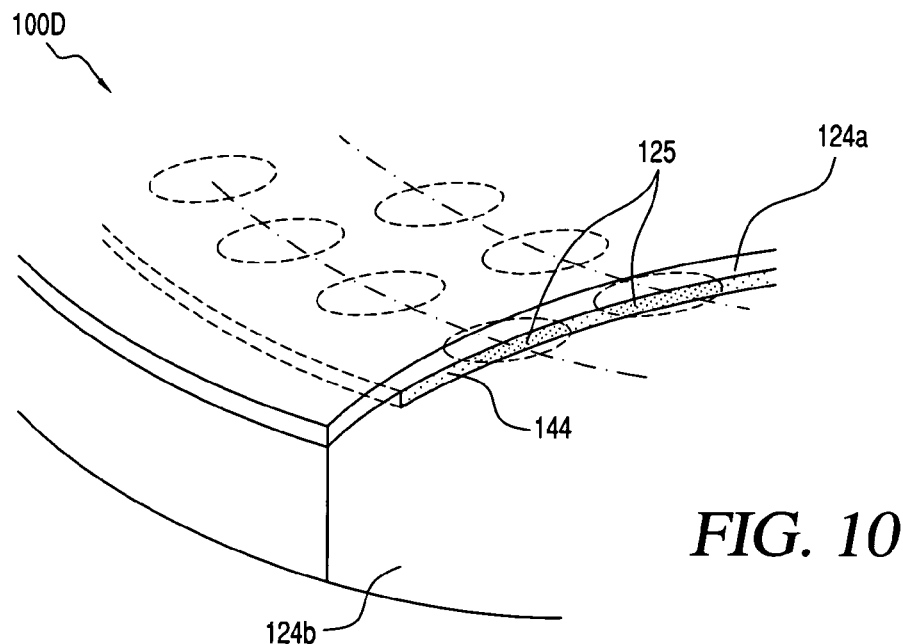
FIG. 10 illustrates an alternative Type "A" adaptive optic wherein the displacement structures are coupled to the flexible lens surface.

FIG. 10 shows an alternative lens 100C that shows the displacement structures 125 being disposed directly onto a lens layer 124a (it then being flipped over) to assemble with base layer 124b. The sealing of lens layers 124a and 124b can be accomplished in various manner such as adhesives or providing cooperating polymer precursors in each layer and thereafter fully polymerizing the assembly. In another method, the displacement structures 125 can be dispensed onto an applanated base layer 124b that is then assembled with fluid layer 144 and lens surface layer 124a.

Figure 11A:
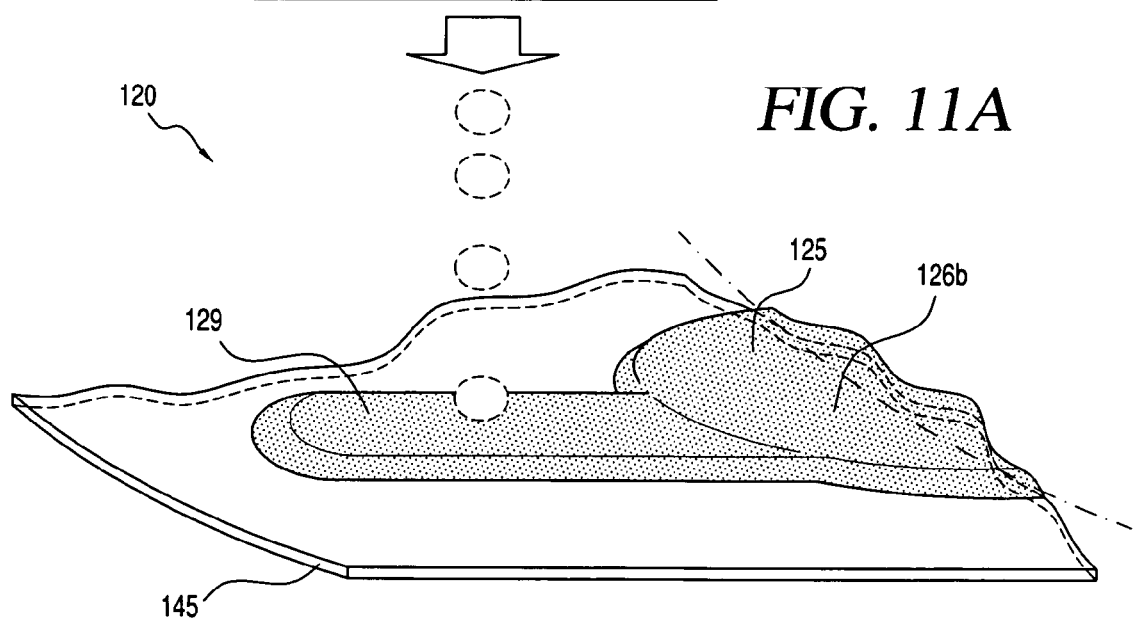
FIG. 11A is an enlarged perspective view of the initial step of making the interior phase and displacement structure of FIG. 6B with a drop-on system.
Figure 11B:
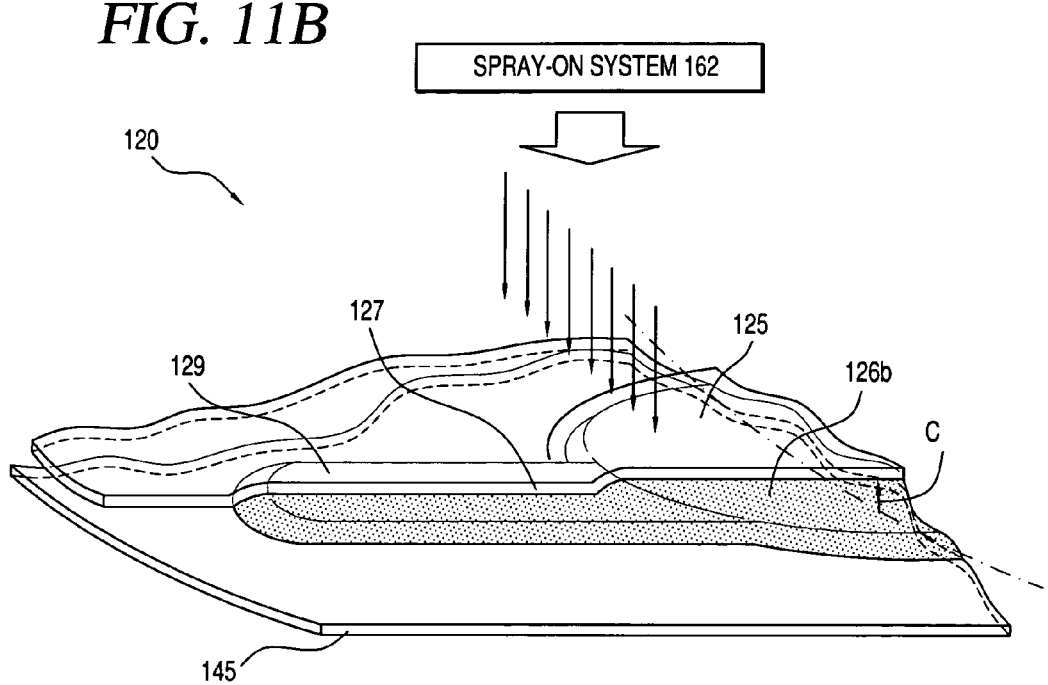
FIG. 11B illustrates the next step of the method of making the interior phase of FIG. 11A wherein a thin film heat shrink polymer is disposed over the displacement structure.
Figure 11C:
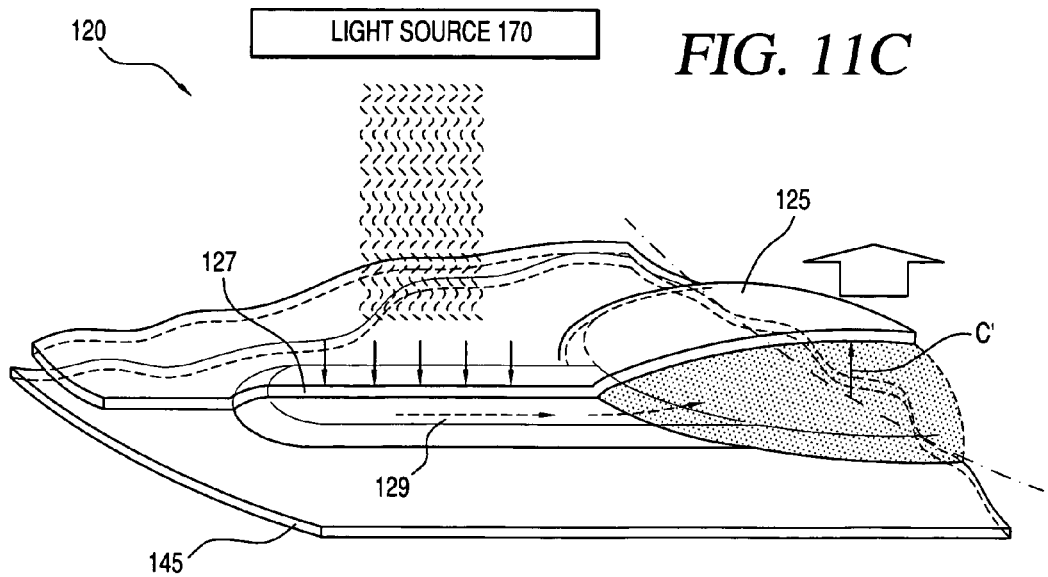
FIG. 11C illustrates the method of utilizing the interior phase and displacement structure of FIG. 6B wherein applied light energy shrinks the heat shrink polymer to actuate the displacement structure.

Now turning to FIGS. 11A-11C, the steps of making and using interior lens phase 120 of lens 100B of FIG. 6B are shown. In FIG. 11A, the drop-on system 160 is used to dispense flowable media 126b onto substrate 145 in a pattern indicates with at least one extending portion 129. In this embodiment, one extending portion 129 is shown but the number can range from 1 to 6 or more.

In one method, a larger volume of media 126b can be dispensed in the central portion with a first surface tension and then (optionally) be irradiated and partly polymerized to increase it surface tension, and thereafter another volume of flowable media 126b can be drop-on dispensed to provide the extending portions 129 at a second surface tension. Thus, the method of the invention included intermediate steps to alter the surface tension of media portions or the use of different index-matched media with different surface tensions to create displacement structure with different portions having different axial heights.

FIG. 11B illustrates the next step of the method wherein a heat-shrink or shape change polymer is sprayed on with system 162 or dispensed using drop-on technology to envelop the flowable media 126b to thereby allow it to flow from the spaces 129 to the more central space portion 125 to displace the overlying lens region 140 exactly as described above in FIG. 9B. In this embodiment, the flowable media 126b can be induced to flow under a photomodifiable polymer capping layer 127 which seals the entire displacement structure 125 in the microfabricated interior phase 120.

In one method depicted in FIG. 11B, the thin layer 127 is fabricated by drop-on or spray dispensing of an index-matched heat shrink polymer precursor over the assembly which is then polymerized into a thin film coating by any suitable means such as UV curing. In another method not shown in the Figures, a cap layer 127 is provided in the form of a thin-film heat-shrink substrate that is sealably formed over the assembly as in FIG. 11B.

FIG. 11C next shows the method of utilizing a laser or light source to actuate the displacement structure 125 by applying light energy to the heat shrink layer 127 in a peripheral extending portion 129 which impinges on the volume therein to displace flowable media 126b to central portion which moves axial height C' from the lesser height C of FIGS. 11B. The heat shrink polymer of FIGS. 11A-11C can thus be defined as a type of pump means to displace flowable media 126b to actuate the displacement structure 125. The interior phase of FIG. 11C would operate to deform a lens surface layer 124b exactly as in FIG. 9B with fluid layer 144 (not shown) again in-filling the region around the actuated displacement structure 125. Thus, for convenience, the steps of illustrating the displacement structure 125 of FIG. 11C together with an overlying deformable lens layer 124a are not provided.

Figure 12A:
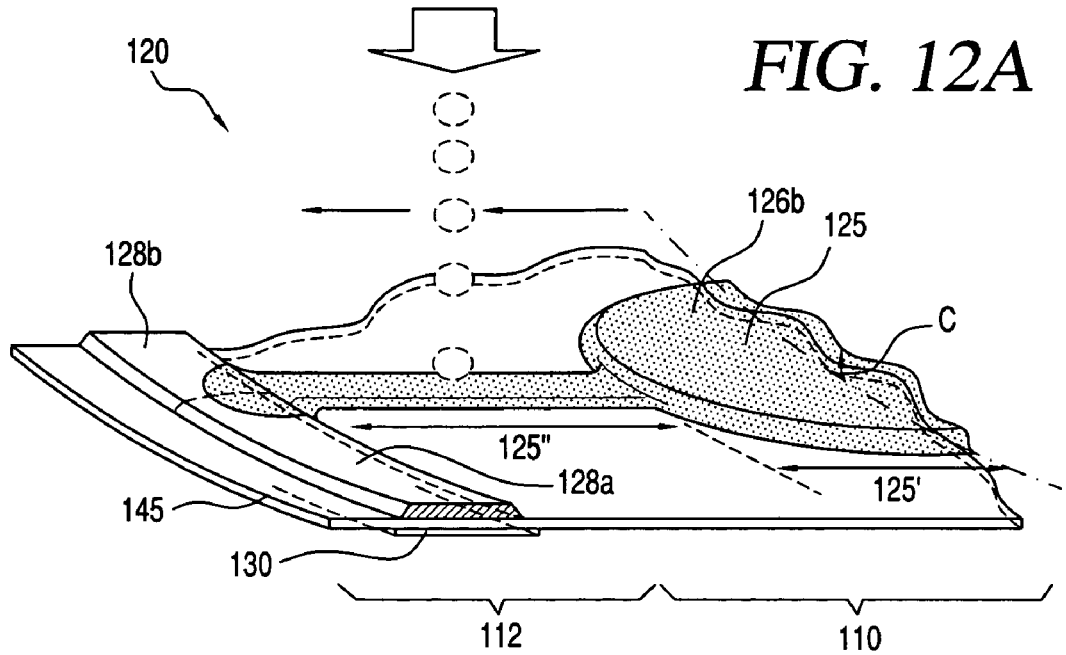
FIG. 12A is an enlarged perspective view of the initial step of making the interior phase and displacement structure of FIG. 6C with a drop-on system.
Figure 12B:
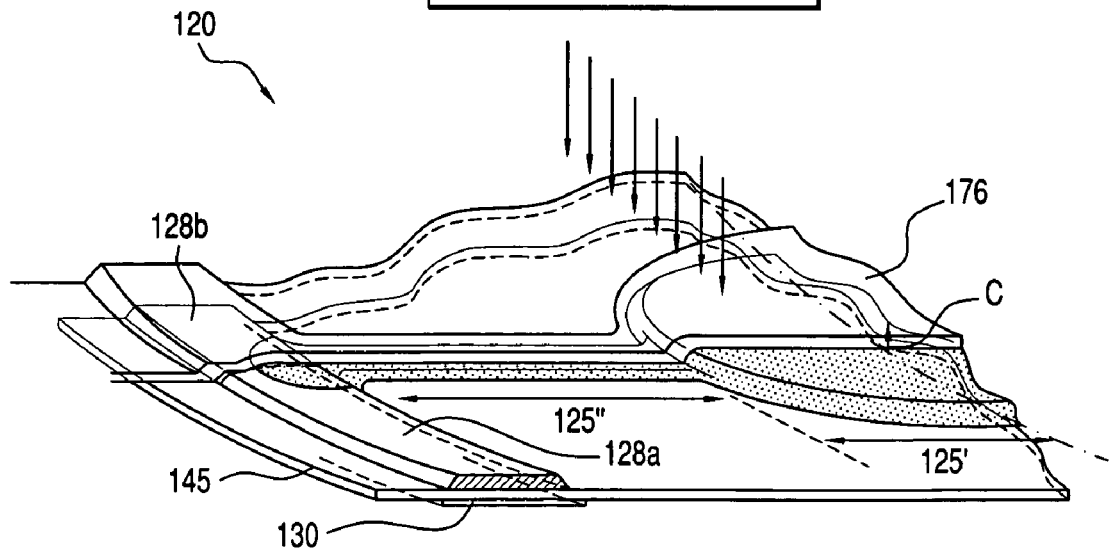
FIG. 12B illustrates the next step of the method of making the interior phase of FIG. 12A wherein a thin film cap layer is disposed over the displacement structure and two shape change polymer components.
Figure 12C:
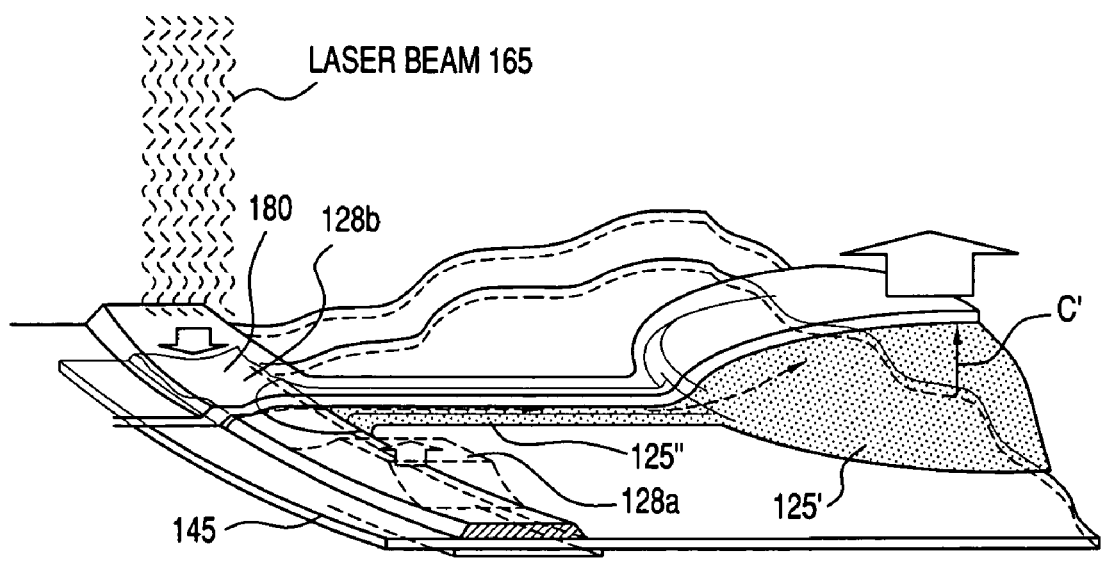
FIG. 12C illustrates the method of utilizing the interior phase and displacement structure of FIG. 6C wherein applied light energy alters multiple shape change polymers to reversibly actuate the displacement structure.

Now turning to FIGS. 12A through 12C, the steps of making and using the interior lens phase 120 of lens 100C of FIG. 6C are is shown. FIG. 12A shows that the non-transmissive layer 130 can be fabricated on substrate 145 by any suitable means such as printing, bonding a non-transmissive annular element or the like. In FIG. 12A, the first and second shape-change polymers 128a and 128b of the displacement structure 125 can be created by drop-on dispensing or another preliminary operation to provide an expandable shape-change polymer 128a portion and a heat shrink polymer portion 128b in a peripheral region 112 of the optic and substrate 145. The shape memory shrink polymer is a foam or CHEM as described above with a potential interior open volume with the SMP structure in a compacted temporary shape.

Upon photothermal modification, the SMP's expansion will draw flowable media 126b into the open interior of the foam network to subtract from the volume of first space portion 125' within the optic portion 110 of the lens to thereby decrease its axial dimension C. The heat shrink polymer structure 128b, for example, is a reticulated, porous, channeled or it can also be a thin-film structure with a single interior lumen-the polymer being in a non-shrunken state in its initial deployed state. Further, the open interior of the heat shrink polymer structure 128b is infused with flowable media 126b in a preliminary operation of by the drop-on dispensing step described next.

FIG. 12A further illustrates the step of the method that is similar to that of FIGS. 7 and 8A wherein a flowable media 126b is drop-on dispensed in and along space 125" to operatively interface with the peripheral substrate region carrying the first and second shape-change polymers 128a and 128b configured thereon. As described in the text accompanying FIGS. 11A-11C, the flowable media 126b can be provided with varying depths and surface tensions.

FIG. 12B next illustrates the fabrication of a cap layer 176 over the entire assembly of the first and second shape-change polymers 128a, 128b and flowable media 126b to seal the volume of exchangeable flowable media therein to provide a photoactuatable displacement structure 125. One method depicted in FIG. 12B is fabricating the thin film cap layer 176 by use of a spray-on system 162 that disperses an index-matched polymer over the assembly which is then polymerized into a thin film coating. As described previously, such a cap layer 176 also can be provided in the form of a thin-film polymer substrate sealably formed over the displacement structure assembly.

FIG. 12C next shows the method of utilizing a laser or light source to actuate the displacement structure 125 by applying light energy to region 180 of the heat shrink polymer portion 128b wherein photothermal absorption cause shrinkage of region 180 to thereby expel flowable media 126b therefrom which in turn drives a flow (see arrows) into space portion 125' to move the structure to a greater axial height C' from the lesser height C of FIG. 12B. The shape change polymer 128b of FIG. 12C functions in effect to pump and displace flowable media 126b to actuate the displacement structure 125 in an axial dimension. This interior phase of FIG. 12C operates to deform a lens surface layer 124b exactly as in FIG. 9B with fluid layer 144 again in-filling the region around the actuated displacement structure 125. For convenience, FIG. 12C does not illustrate the lens surface layer 124b and intermediate fluid layer 144.

FIG. 12C also depicts in phantom view the method of utilizing applied light energy to reversible actuate the displacement structure 125 by applying light energy to region to a region of shape memory polymer portion 128a wherein the photothermal effect therein causes expansion of local region 182 to thereby draw flowable media 126b into the open interior of the polymer 128a to thereby reduce the axial height of the space 125.

Thus, the invention provides for reversible actuation of the displacement structure 125. It can be appreciated that the system can be utilized to reversibly actuate the displacement structure 125 to alter its axial amplitude a number of times determined by the dimensions and volume of the shape change polymer portions 128a and 128b. By this means, the lens region 140 overlying each actuator can be reversibly actuated and provided with a known maximum range of amplitude for correction of wavefront aberrations or together with a plurality of other actuators to alter the spherical shape of the lens.

Figure 13A:
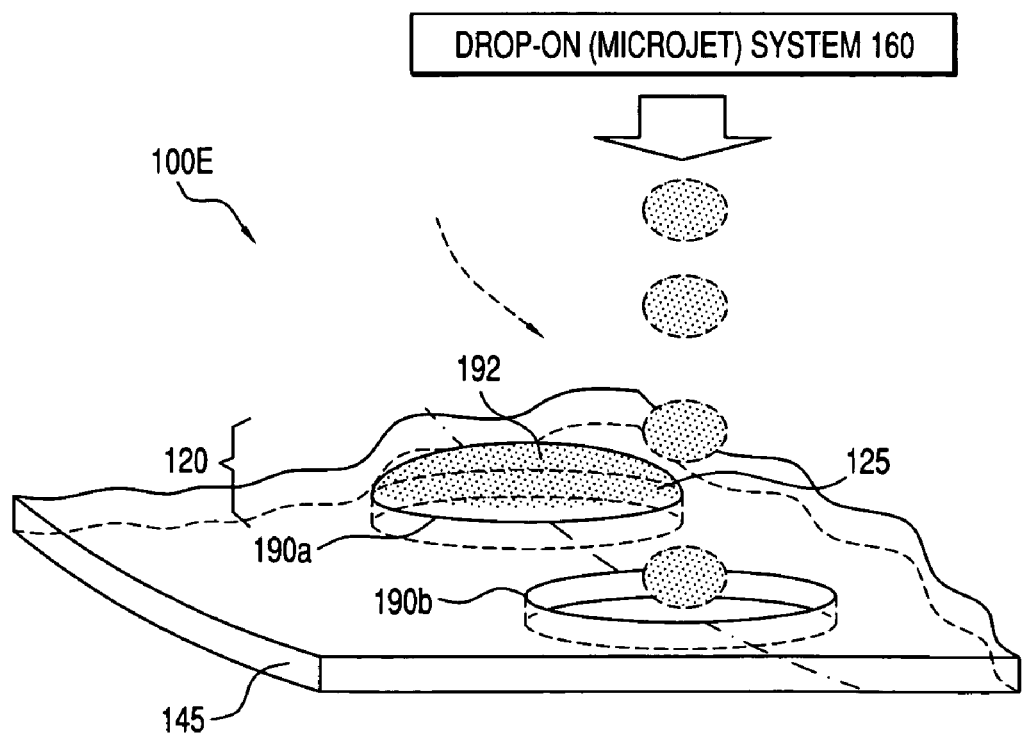
FIG. 13A is a perspective view of the initial step of making an alternative adaptive interior phase and displacement structures with a drop-on system into microfabricated wells in a substrate.
Figure 13B:
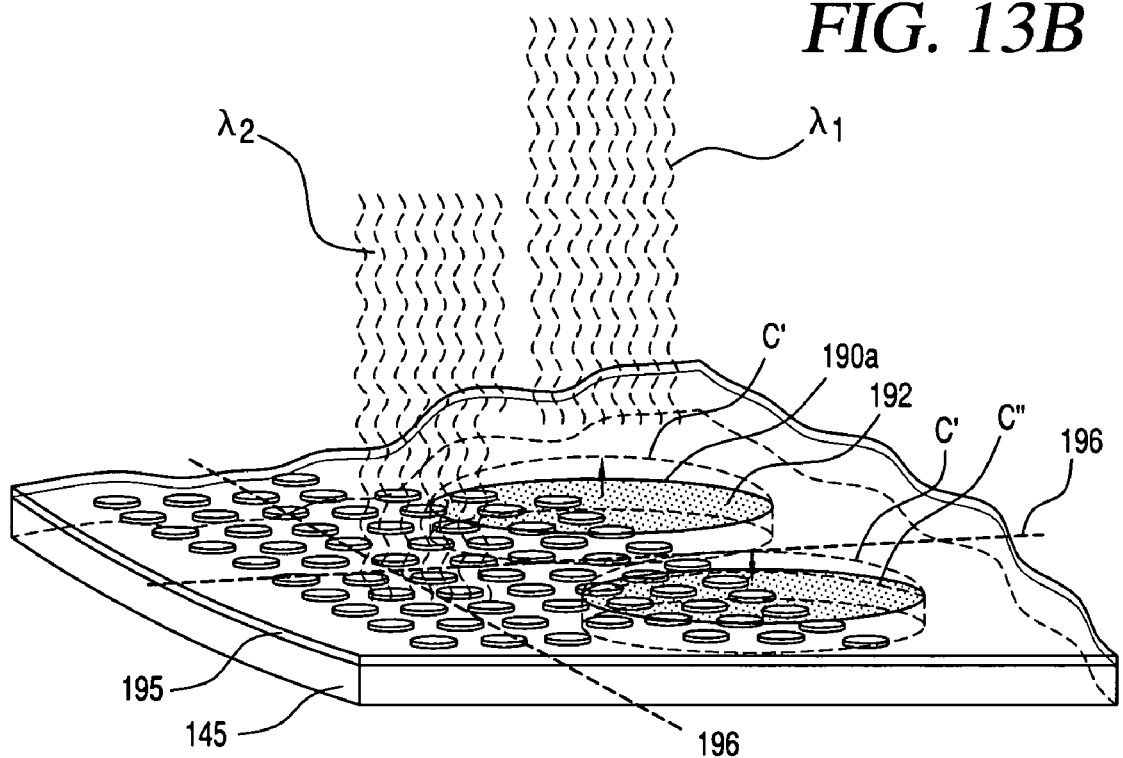
FIG. 13B illustrates the next step of the method of making the interior phase of FIG. 13A wherein a thin film fluid permeable heat shrink cap layer is disposed over the displacement structures.

FIGS. 13A and 13B illustrate an alternative Type "A" embodiment of adaptive optic 100E wherein the interior adaptive phase 120 comprises a substrate 145 with displacement structures or spaces 125 that are formed in microfabricated wells 190 (collectively) with two such wells 190a and 190b depicted. The substrate also can be either the anterior or posterior lens body layers 124a and 124b as in FIG. 2.

FIG. 13A illustrates the wells 190 being filled with a drop-on dispensing system 160 with a shape memory polymer foam media 192 being dispensed therein with the media having substantial surface tension to provide a highly bulged memory shape relative to the surface of the substrate. FIG. 13B next illustrates several steps of making and using the interior phase 120. First, the shape memory polymer media 192 structures are all compacted to a stressed temporary shape which conforms with the surface of substrate 145.

FIG. 13B also illustrates the placement and bonding of a thin film 195 to substrate 145 over the displacement structures 125. The bonding can be completely across the substrate or along lines indicated at 196 that are spaced apart from the shape memory polymer media 192. In a method of use, it can be understood that the media 192 in well 190a can be expanded by photothermal absorption from a first wavelength indicated at $\lambda_1$ to an increased axial height indicates at C'. It also can be understood that irradiation of heat shrink thin film 195 can cause contraction of the expanded SMP foam as indicated in well 190b in FIG. 13B wherein the structure's height may be altered from C' to at C".

Preferably, a second wavelength indicated at $\lambda_2$ is used for the irradiation of the heat shrink polymer. In an alternative embodiment, the glass transition temperature of the SMP and the shrink temperature of the film can differ to allow different heat levels to actuate the displacement structures 125 in opposing directions.

The scope of the invention and the method of making an adaptive optic includes the drop-on microjet dispensing of precise polymer volumes in microfabricated wells of any lens component, as in the any of the displacement structure types of FIGS. 2, 4, 5, 6A-6C and 10.

3. Type "B" Adaptive Optic System.

Figure 14:
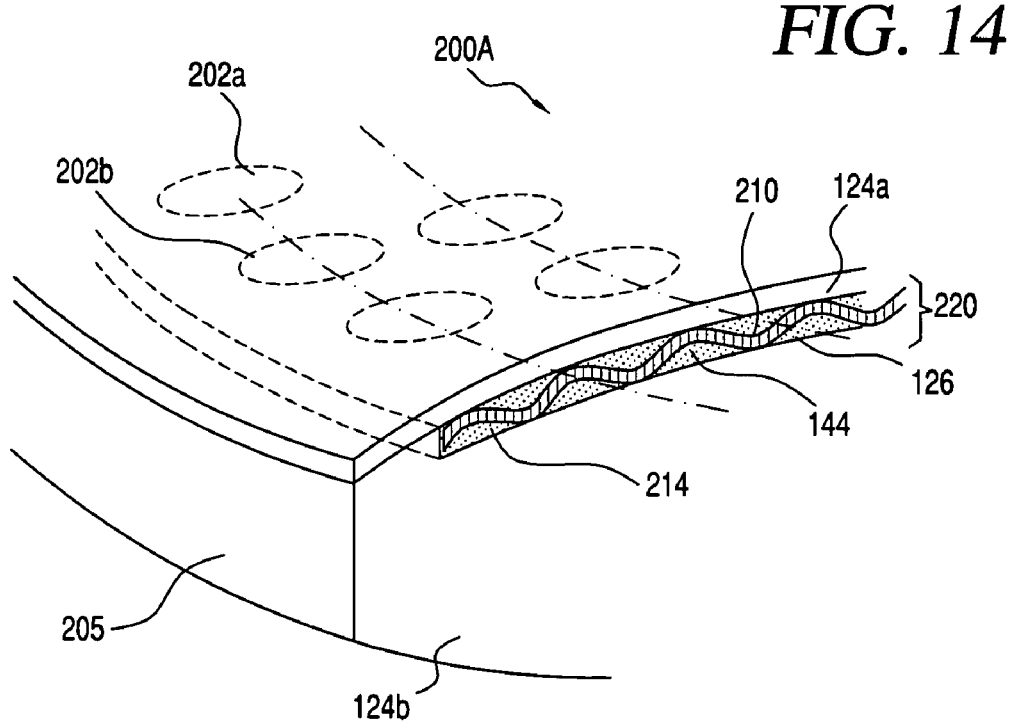
FIG. 14 illustrates a Type "B" adaptive optic with an alternative interior phase that is coupled to the flexible lens surface.
Figure 15A:
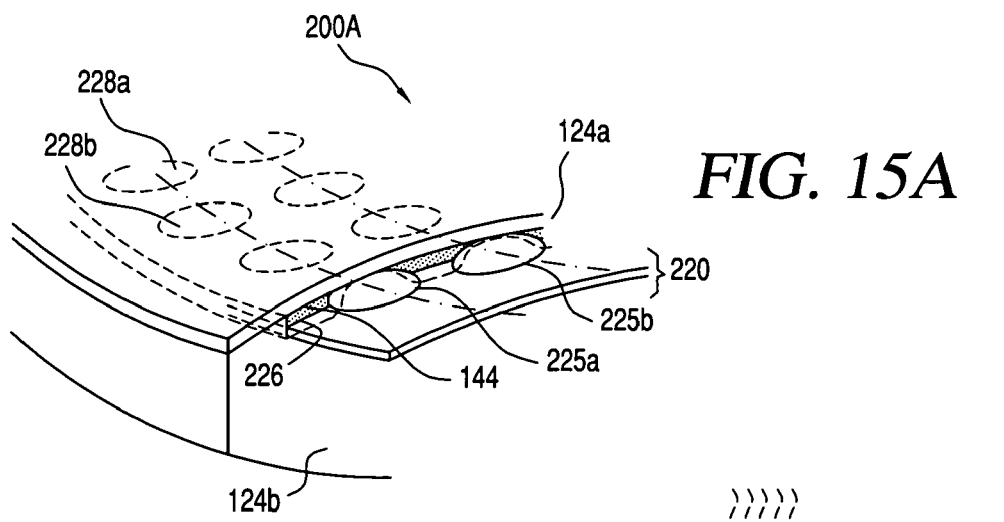
FIG. 15A illustrates an alternative Type "B" adaptive optic with an alternative interior phase.
Figure 15B:
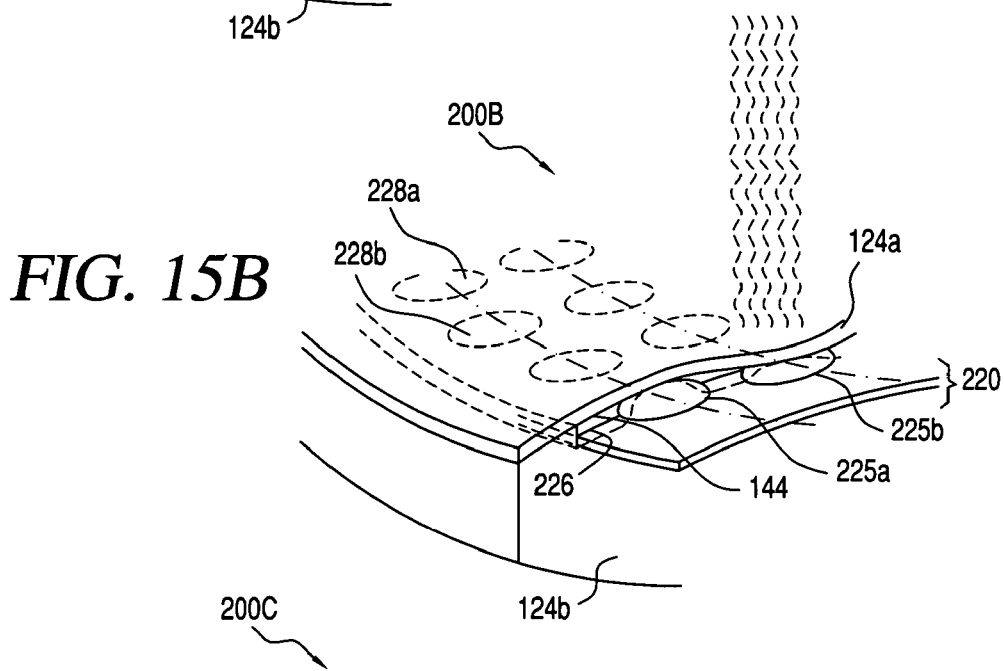
FIG. 15B illustrates the alternative interior phase of FIG. 15A after being actuated.

FIGS. 14 and 15A-15B illustrate an alternative adaptive optic 200A that can be understood by the cut-away view of only an edge portion of the lens body 205. In this embodiment, the interior phase 220 is of a resilient index matched porous heat shrink polymer form indicated at 222. The form 222 has concentric formed undulations 225a therein wherein the anterior and posterior peaks of the undulations are bonded to the first and second lens body layers 124a and 124b.

The lateral space 226 that contains the interior phase 220 is filled again with index matched fluid 144 as in the Type "A" embodiments above (with the peripheral expansion space for fluid 144 not shown). The structure of the undulation 225a is sufficiently resilient to maintain the space 226 in an open position as in FIG. 14 after unfolding deployment. It can be easily understood that the interior phase 220 can be irradiated at predetermined locations or addresses 228a, 228b etc. at the surface layer to shrink the polymer to thereby inwardly displace the surface layer to cause power adjustment (cf. FIG. 15B). In this adaptive optic type, the lens would be implanted with an over steep curvature and the interior phase is adapted to reduce curvature.

FIGS. 15A and 15B illustrate an alternative embodiment wherein the interior phase 220 again is of a resilient index matched porous heat shrink material but with formed domes 225b rather than undulations as in FIG. 14. The scope of the invention thus covers any resilient interior phases 220 that define surface relief for maintaining spacing across interior space 226. The anterior dome surfaces are bonded to the anterior layer 124a so that contraction of the dome will actuate and depress the region of the surface layer overlying the structure 225b upon irradiation as depicted in FIG. 15B. In effect, the actuator functions in the opposite manner of that of the Type "A" embodiment.

Figure 15C:
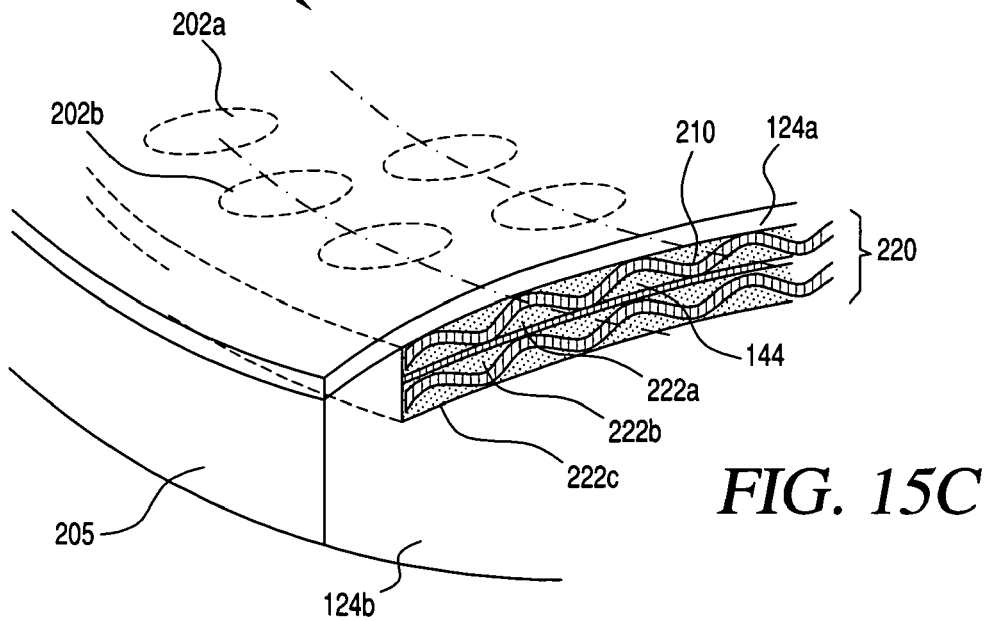
FIG. 15C illustrates an alternative adaptive optic similar to FIG. 14 but with overlapping interior phases for smoothing the lens surface curvature after independent actuation of structures in separate phases.

FIG. 15C illustrates an adaptive optic with three interior phases 222a-222c that overlap to allow for smooth change in surface radii. Of particular interest, one phase can be adapted apply positive vertical forces, and a second phase can be adapted to subtract from vertical forces for a reversible system. Also, the fluid in the interior phases can of a type that can be fully polymerized by any type of photo-curing after distribution among the displacement structures to set a final shape.

Figure 16A:
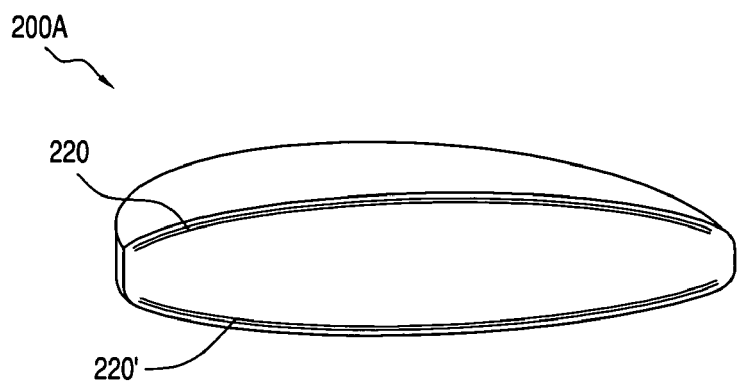
FIGS. 16A-16B illustrate any adaptive optic of the invention with locations of a plurality of interior phases.
Figure 16B:
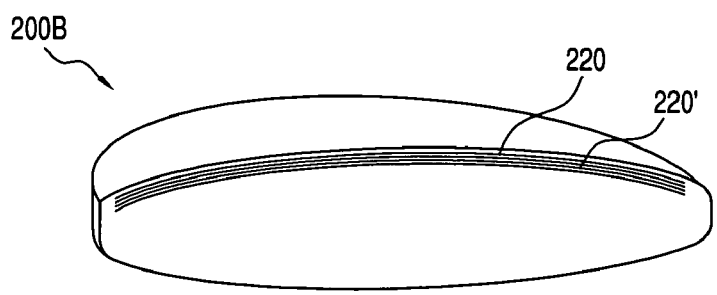

Without repeating the drawings of the Types "A" and "B" embodiments above, it can be easily understood that first and second interior phases 220 and 220' of the Types "A" and "B" displacement systems, respectively, can be combined to provide a reversible actuation system. FIGS. 16A and 16B illustrate such a lens 200B with the dual phases 220 and 220' in an anterior location and in spaced apart locations.

4. Type "C" Adaptive Optic System.

Figure 17:
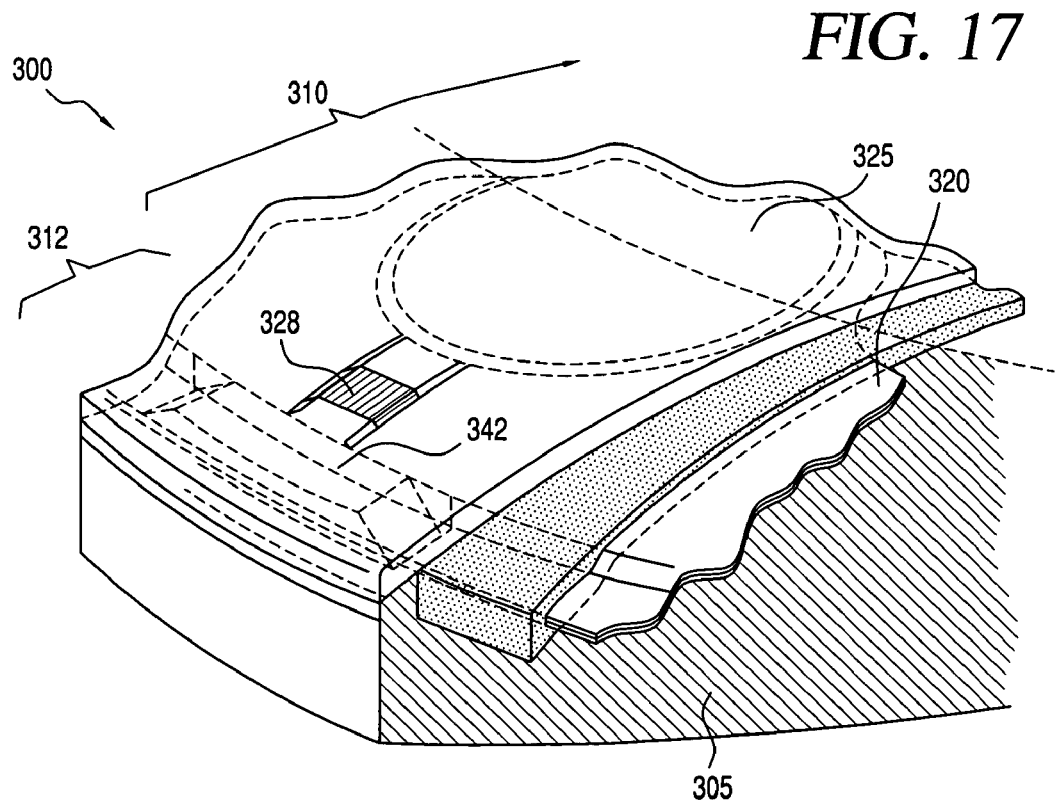
FIG. 17 is an adaptive optic of the invention with a photothermally sacrificial valve.

FIG. 17 illustrates an alternative adaptive optic 300 that can be understood again by the cut-away view of the peripheral portion of the lens body 305. In this embodiment, the interior phase 320 again carries a plurality of fluid-filed displacement structures indicated at 325. Each such structure is somewhat pressurized after the lens is implanted due to intraocular pressure.

The peripheral region of the lens has a sacrificial valve 328 or a controllable release valve that can be photothermally actuated to release fluid media 340 from each displacement structure 325 wherein the fluid will flow to an internal chamber collapsed flexible sac chamber 342 in the lens periphery. In substance, this system functions approximately as the Type "A" embodiment wherein a collapsed porous SMP structure is photothermally altered to allow fluid flow therein or therethrough.

Without repeating the drawings of the Type "A" embodiments above, it can be easily understood the displacement structure types of FIGS. 6A-6C in an interior phases 120 can be combined with the sacrificial valve 328 or a controllable release valve of FIG. 17 to provide a reversible actuation system.

5. Type "D" Adaptive Optic and Method of Making.

Figure 18A:
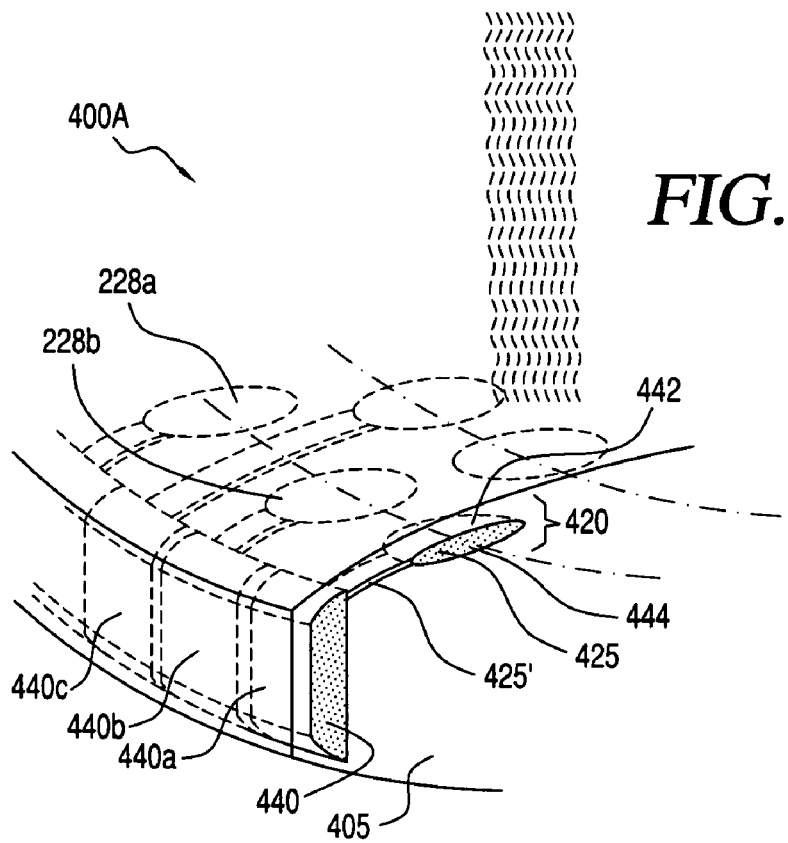
FIGS. 18A-18B illustrate an adaptive optic with a plurality of overlapping interior phases that utilize the displacement structures of FIGS. 3C-3F.
Figure 18B:
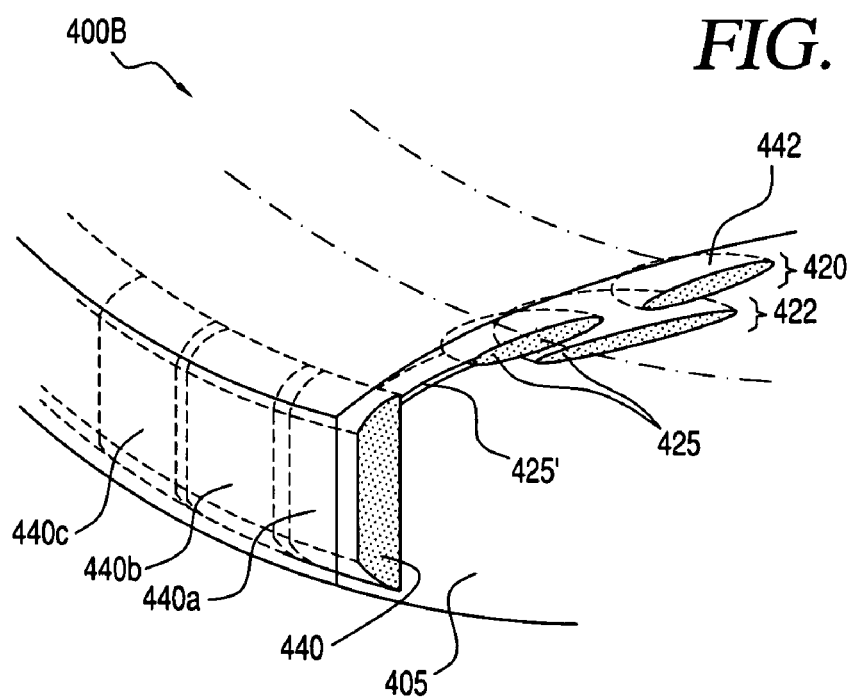

FIGS. 18A and 18B illustrate an alternative adaptive optic 400A, showing only cut-away views of the peripheral portion of an exemplary lens body 405 of a resilient hydrogel, acrylic, silicone or other similar material. This lens embodiment again carries a plurality of fluid-filed displacement structures or spaces indicated at 425 identifiable as addresses 228a, 228 etc. at the lens surface. This lens differs in its method of fabrication. In this embodiment, the lens body is fabricated by molding, casting or turning and polishing or in any other manner known in the art of IOL fabrication to provide a finished lens body having a known power and shape. In other words, this lens can be made by starting essentially with an off-the-shelf lens. As will be described below an additional peripheral shape change polymer component 440 is required.

FIG. 18A illustrates the method of fabricating the spaces 425 in the lens body to provide a thin resilient deformable layer 442 over each space 425. In FIG. 18A, a femtosecond laser as known in the art is focused to deposit energy in an inner layer of the plane or phase 420 of lens body 405 in a very short time interval such as fs or ps. As the energy is transferred from the laser beam, a plasma formation occurs and the material is removed or ablated to create a space 425.

In the lens material, the distance over which the heat due to laser energy is dispersed is less than the absorption length of the laser, thereby allowing volumetric removal of material before energy losses due to thermal diffusion can occur and overheat the polymer. The science of utilizing femtosecond is well established and need not be described further. It can be seen in FIG. 18A that this approach can microfabricate spaces 425 and channels portions 425' of the spaced that extend to a peripheral non-optic portion 112 of the lens body. After fabrication of the lens, the interior spaces and channels are flushed and filled with a fluid 444 that is index-matched to the lens body to re-occupy the spaces 425 and the lens will then have its original shape and power.

In order to alter the lens shape, any polymer shape adjustable system as illustrated in FIG. 6C is utilized to cause fluid flows into or out of the chambers by irradiation of the targeted polymer indicated at 440 in any sub-pattern of locations 440a, 440b, 440c etc. in the lens periphery that are fluidly coupled to each space 425. FIG. 18B illustrates an alternative lens 400B which is in all respects similar to the lens of FIG. 18A except that the adaptive spaces 425 are carried in a plurality of interior phases or layers 420 and 420' wherein the spaces are offset from one another wherein independent actuation of various phases will allow for the creation of substantially smooth lens surface curvatures.

The scope of the invention extends to microfabrication of an adaptive optic with a plurality of interior phases or layers by conventional molding or casting and assembly techniques known in the art.

The scope of the invention extends to microfabrication of an adaptive optic by creating a porous polymer block monolith in the shape of a lens wherein the pore are filled with an index-matched fluid media and wherein the body portion are globally polymerized and by photo-curing with a scanned focused light energy delivery to fully polymerized the entire lens block with the exception of spaces and channels that extend to any of the displacement structures of FIGS. 3A-3J and 18A-18B that are assembled within or bonded to the optic's periphery.

The scope of the invention extends to any adaptive optic that has media displacement means coupled to each interior space as in FIG. 2 that comprises a non-mechanical pump selected from the class of electroosmotic, electrohydrodynamic and magnetohydrodynamic pump systems as are known in the art. The scope of the invention extends to any adaptive optic that has media displacement means coupled to each interior space as in FIG. 2 that comprises a mechanical pump selected from the class of thermohydraulic micropump systems, thermopneumatic-assisted pump systems, and thermoperistaltic systems.

In any of the above-described embodiments, the intraocular lens can be combined with a wavefront sensing system (e.g. a Shack Hartman system) to allow computer-controlled correction of the aberrations in the adaptive optic of the invention.

The scope of the invention extends to any adaptive optic as described above for non-ophthalmic uses. For example, an adaptive optic can be developed with a resilient lens body have at least one interior phase with each of the plurality of displacement structures (actuators) comprising a space filled with an index matched fluid therein. Each displacement structure is coupled to a fluid-filled peripheral space, fluid source (or remote chamber) outside the lens optic portion that is coupled to a real-time computer controller to control the volume and pressure of each displacement structure in the interior lens phase to modulate lens shape at a high repetition rate.

Such an adaptive optic can be readily fabricated with microfluidic channels and pumps, controllers and a wavefront sensor for wavefront correction in imaging and beam forming systems for optical communications, biomedical imaging, astronomical instruments, military laser focusing, aviation and aerodynamic control, laser beam and cavity control and laser welding and other similar uses. The lens generally is represented in FIG. 2. It is postulated that such an adaptive optic can be microfabricated economically and be far more robust for certain operating environments than micro-mirror arrays and lenses that are being developed and known in the art.

Those skilled in the art will appreciate that the exemplary embodiments and descriptions thereof are merely illustrative of the invention as a whole, and many variations may be made within the spirit and scope of the invention. Specific features of the invention may be shown in some figures and not in others, and this is for convenience only and any feature may be combined with another in accordance with the invention.

What is claimed is:

1. A lens for vision correction comprising a lens body defining a peripheral non-optic portion and a central optic portion having an optical axis, the peripheral non-optic portion including a shape memory polymer (SMP) and the central optic portion excluding a SMP.

2. A lens as in claim 1 wherein the SMP has a memory shape and is self-maintainable in a different temporary shape, and wherein the SMP is moveable from the temporary shape toward the memory shape in response to a stimulus.

3. A lens as in claim 2 wherein the stimulus is heat.

4. A lens as in claim 2 wherein the SMP includes a chromophore for cooperating with a selected light wavelength.

5. A lens as in claim 4 wherein the stimulus is energy from irradiation by the selected light wavelength.

* * * * *